US010300476B2

(12) United States Patent
Alvez-Manoli

(10) Patent No.: US 10,300,476 B2
(45) Date of Patent: *May 28, 2019

(54) METHODS OF REGENERATING AROMATIZATION CATALYSTS WITH A DECOKING STEP BETWEEN CHLORINE AND FLUORINE ADDITION

(71) Applicant: Chevron Phillips Chemical Company LP, The Woodlands, TX (US)

(72) Inventor: Gabriela D. Alvez-Manoli, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/597,189

(22) Filed: May 17, 2017

(65) Prior Publication Data

US 2018/0333713 A1 Nov. 22, 2018

(51) Int. Cl.
| | | |
|---|---|---|
| *C10G 35/095* | (2006.01) | |
| *C07C 5/41* | (2006.01) | |
| *B01J 38/46* | (2006.01) | |
| *B01J 38/12* | (2006.01) | |
| *B01J 29/62* | (2006.01) | |
| *B01J 29/90* | (2006.01) | |
| *B01J 38/42* | (2006.01) | |
| *C10G 35/085* | (2006.01) | |
| *B01J 38/48* | (2006.01) | |
| *B01J 38/04* | (2006.01) | |
| *B01J 38/44* | (2006.01) | |
| *B01J 29/60* | (2006.01) | |
| *C10G 35/04* | (2006.01) | |
| *C10G 35/06* | (2006.01) | |

(52) U.S. Cl.
CPC ............... *B01J 38/12* (2013.01); *B01J 29/60* (2013.01); *B01J 29/62* (2013.01); *B01J 29/90* (2013.01); *B01J 38/04* (2013.01); *B01J 38/42* (2013.01); *B01J 38/44* (2013.01); *B01J 38/46* (2013.01); *B01J 38/48* (2013.01); *C07C 5/412* (2013.01); *C07C 5/415* (2013.01); *C07C 5/417* (2013.01); *C10G 35/04* (2013.01); *C10G 35/06* (2013.01); *C10G 35/085* (2013.01); *C10G 35/095* (2013.01); *C07C 2529/068* (2013.01); *C07C 2529/62* (2013.01)

(58) Field of Classification Search
CPC ... B01J 38/04; B01J 38/12; B01J 38/42; B01J 38/44; B01J 38/46; B01J 38/48; C10G 35/04; C10G 35/06; C10G 35/085; C10G 35/095; C07C 2529/62; C07C 2529/068; C07C 5/417; C07C 5/415; C07C 5/412
USPC ...... 502/22, 32, 35, 36, 37, 38, 50; 208/135, 208/138, 139, 140
See application file for complete search history.

(56) References Cited

U.S. PATENT DOCUMENTS

| | | | |
|---|---|---|---|
| 2,906,702 A | 9/1959 | Brennan et al. | |
| 3,898,173 A * | 8/1975 | Hayes | B01J 23/96 208/140 |
| 4,456,527 A | 6/1984 | Buss et al. | |
| 4,810,683 A | 3/1989 | Cohn et al. | |
| 4,937,215 A | 6/1990 | Murakawa et al. | |
| 5,155,074 A | 10/1992 | Mohr | |
| 5,196,631 A | 3/1993 | Murakawa et al. | |
| 5,260,238 A | 11/1993 | Murakawa et al. | |
| 5,389,235 A | 2/1995 | Russ et al. | |
| 5,401,365 A | 3/1995 | Chen et al. | |
| 5,401,386 A | 3/1995 | Morrison et al. | |
| 5,866,743 A | 2/1999 | Heyse et al. | |
| 6,121,180 A * | 9/2000 | Gevelinger | B01J 38/44 502/34 |
| 6,190,539 B1 | 2/2001 | Holtermann et al. | |
| 6,207,042 B1 | 3/2001 | Holtermann et al. | |
| 6,406,614 B1 | 6/2002 | Tiedtke et al. | |
| 6,518,470 B1 | 2/2003 | Fukunaga et al. | |
| 6,548,030 B2 | 4/2003 | Heyse et al. | |
| 6,812,180 B2 | 11/2004 | Fukunaga | |
| 7,153,801 B2 | 12/2006 | Wu | |
| 7,544,335 B2 | 6/2009 | Scanlon et al. | |
| 7,582,272 B2 | 9/2009 | Glova et al. | |
| 7,932,425 B2 | 4/2011 | Blessing et al. | |
| 8,119,203 B2 | 2/2012 | Hise et al. | |
| 8,716,161 B2 | 5/2014 | Wu | |
| 8,912,108 B2 | 12/2014 | Wu | |
| 9,085,736 B2 | 7/2015 | Morrison et al. | |
| 2010/0160147 A1* | 6/2010 | Wu | B01J 23/96 502/29 |
| 2013/0231512 A1* | 9/2013 | Wu | B01J 29/90 585/407 |
| 2014/0213839 A1* | 7/2014 | Wu | B01J 38/46 585/419 |
| 2015/0073190 A1* | 3/2015 | Wu | B01J 29/90 585/419 |
| 2016/0045904 A1* | 2/2016 | Wu | B01J 29/90 585/419 |

\* cited by examiner

*Primary Examiner* — Elizabeth D Wood
(74) *Attorney, Agent, or Firm* — Merchant & Gould P.C.

(57) ABSTRACT

Methods for regenerating a spent catalyst in a metal reactor are disclosed. Such methods may employ a step of chlorinating the spent catalyst, followed by decoking the chlorinated spent catalyst, and then fluorinating the de-coked catalyst.

24 Claims, 10 Drawing Sheets

METHODS OF REGENERATING AROMATIZATION CATALYSTS WITH A DECOKING STEP BETWEEN CHLORINE AND FLUORINE ADDITION

FIELD OF THE INVENTION

The present disclosure concerns methods for the regeneration of spent catalysts, and more particularly relates to the regeneration of spent catalysts containing a transition metal, such as platinum, and a catalyst support.

BACKGROUND OF THE INVENTION

The catalytic conversion of non-aromatic hydrocarbons into aromatic compounds, often referred to as aromatization or reforming, is an important industrial process that may be used to produce benzene, toluene, xylenes, and the like. The aromatization or reforming process often is conducted in a reactor system that may contain one or more reactors containing transition metal based catalysts. These catalysts may increase the selectivity to and/or the yield of the desired aromatic compounds. However, under commercial reaction conditions, these catalysts slowly lose their activity, often indicated by a loss of selectivity to desired aromatic compounds and/or a reduction in conversion rates. Such catalysts are often referred to as "spent" catalysts once economic or operational thresholds are passed.

Because of their commercial importance and the expense incurred in producing fresh catalyst to replace spent catalyst, there is an ongoing need for improved methods of restoring catalytic activity to spent aromatization catalysts. Accordingly, it is to this end that the present disclosure is generally directed.

SUMMARY OF THE INVENTION

Methods for regenerating spent catalysts comprising a transition metal and a catalyst support are disclosed and described herein. One such method for regenerating a spent catalyst in a metal reactor may comprise (1) contacting the spent catalyst with a chlorine-containing stream comprising a chlorine-containing compound to produce a chlorinated spent catalyst; (2) contacting the chlorinated spent catalyst with a decoking gas stream comprising oxygen to produce a de-coked catalyst; and (3) contacting the de-coked catalyst with a fluorine-containing stream comprising a fluorine-containing compound.

Another method for regenerating a spent catalyst in a metal reactor consistent with this disclosure may comprise (i) contacting the spent catalyst with a chlorine-containing stream comprising a chlorine-containing compound to produce a chlorinated spent catalyst; (ii) contacting the chlorinated spent catalyst with a chlorine purging stream comprising an inert gas; (iii) contacting the chlorinated spent catalyst with a decoking gas stream comprising oxygen to produce a de-coked catalyst; (iv) contacting the de-coked catalyst with a fluorine-containing stream comprising a fluorine-containing compound to produce a de-coked and fluorinated catalyst; and (v) contacting the de-coked and fluorinated catalyst with a fluorine purging stream comprising an inert gas, which may be the same as or different from the inert gas used in step (ii), for example, nitrogen.

Also disclosed herein are various processes for reforming hydrocarbons. An illustrative process may comprise (A) contacting a hydrocarbon feed with an aromatization catalyst comprising a transition metal and a catalyst support under reforming conditions in a metal reactor system to produce an aromatic product; (B) performing step (A) for a time period sufficient to form a spent catalyst; (C) contacting the spent catalyst with a chlorine-containing stream comprising a chlorine-containing compound to produce a chlorinated spent catalyst; (D) contacting the chlorinated spent catalyst with a decoking gas stream comprising oxygen to produce a de-coked catalyst; and (E) contacting the de-coked catalyst with a fluorine-containing steam comprising a fluorine-containing compound.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DEFINITIONS

Figure 1A:
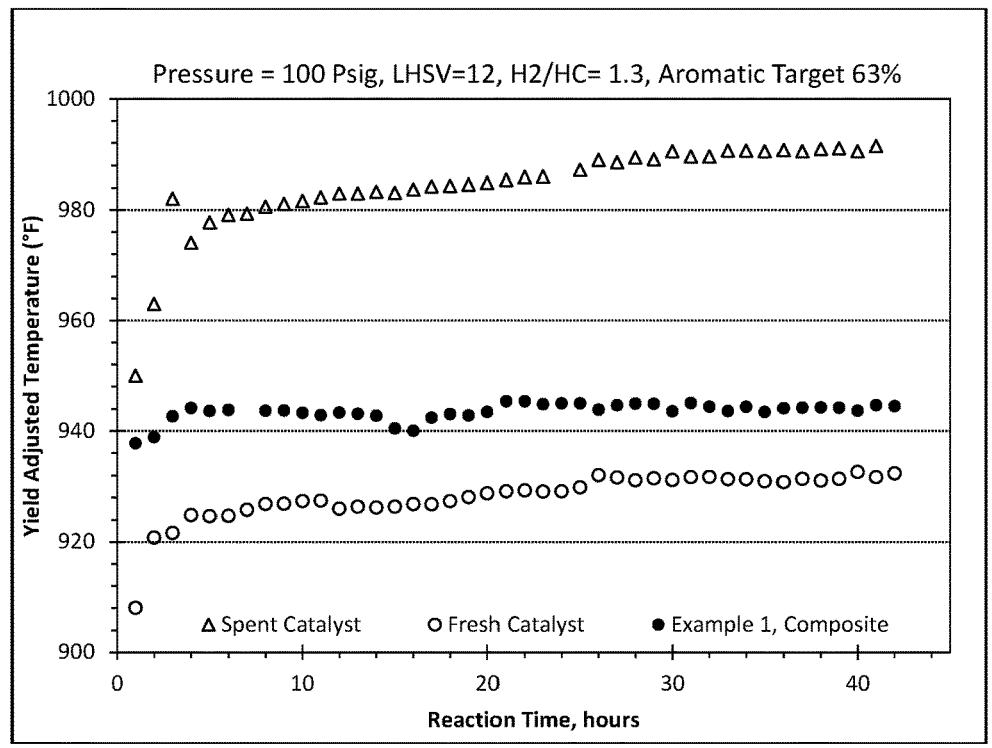
FIG. 1A presents a plot of the yield adjusted temperature versus reaction time for the regenerated catalyst of Example 1, compared with the fresh catalyst and spent catalyst.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), may be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features may be envisioned. For each and every aspect and each and every feature disclosed herein, all combinations that do not detrimentally affect the designs, compositions, processes, or methods described herein are contemplated with or without explicit description of the particular combination. Additionally, unless explicitly recited otherwise, any aspect or feature disclosed herein may be combined to describe inventive designs, compositions, processes, or methods consistent with the present disclosure.

In this disclosure, while compositions and methods are often described in terms of "comprising" various components or steps, the compositions and methods may also "consist essentially of" or "consist of" the various components or steps, unless stated otherwise.

The terms "a," "an," and "the" are intended to include plural alternatives, e.g., at least one. For instance, the disclosure of "a transition metal" or "a chlorine-containing compound," is meant to encompass one, or mixtures or combinations of more than one, transition metal or chlorine-containing compound, unless otherwise specified.

Various catalysts are described herein. A "spent" catalyst generally refers to a catalyst that has unacceptable performance in one or more of catalyst activity, hydrocarbon feed conversion, yield to a desired product(s), selectivity to a desired product(s), or an operating parameter, such as output/production rate or reforming temperature, although the determination that a catalyst is "spent" is not limited only to these features. In some aspects, the "fresh" catalyst may have an activity X, the "spent" catalyst may have an activity Z, and a "regenerated" catalyst or a "reactivated" catalyst may have an activity Y, such that Z<Y<X. Such catalyst activity comparisons (and other reforming performance characteristics) are meant to use the same production run (batch) of catalyst, tested on the same equipment, and under the same test method and conditions. The "regenerated" catalyst encompasses catalysts regenerated using—at a minimum—the chlorination step, the decoking step, and the fluorination step described herein, while the "reactivated" catalyst is the "regenerated" catalyst that has been subjected to a reduction step (e.g., using hydrogen). As would be recognized by one of skill in the art in view of this disclosure, the "regenerated" catalyst is a generic term; it includes a catalyst that has been chlorinated, de-coked, and fluorinated, but also encompasses catalysts that have been subjected to one or more of any other catalyst regeneration steps disclosed herein, such as a chlorine purging step after chlorination, an oxygen purging step after the decoking step, a fluorine purging step after fluorination, and so forth, as well as any combination thereof.

The amounts of any components or materials present on the catalysts described herein (e.g., fresh catalyst, spent catalyst, regenerated catalyst, or reactivated catalyst) are on a weight basis, such as wt. % or ppmw (ppm by weight), unless otherwise specified. These components or materials may include, for instance, the amount of carbon, the amount of fluorine, the amount of chlorine, the amount of platinum, and so forth. Moreover, these amounts are based on a "dry" catalyst, wherein the respective catalyst (e.g., fresh catalyst, spent catalyst, regenerated catalyst, or reactivated catalyst) has been dried to a solvent/water content of less than 10 wt. %.

A "metal reactor" refers to any vessel (or vessels) capable of being used in a catalyst regeneration process, as described herein, that contains a metal material. The metal reactor may contain any suitable metal material (as opposed to a reactor or vessel constructed only of non-metal materials such as glass or quartz, and the like), non-limiting examples of which may include austenitic stainless steels, including 304, 316, 321, 347, 410S, 600, or 800 stainless steel, and the like. Moreover, a coating or layer containing any suitable material, compound, alloy, or metal, such as tin, may be used on any reactor/vessel surface, and the coating or layer may provide resistance to carburization and metal dusting. Representative suitable metal materials and protective layer materials that may be used in the "metal reactor" consistent with this invention are disclosed in U.S. Pat. Nos. 5,866,743, 6,548,030, 8,119,203, and 9,085,736, which are incorporated herein by reference in their entirety.

The metallurgical terms used herein are to be given their common metallurgical meanings as set forth in THE METALS HANDBOOK of the American Society of Metals, incorporated herein by reference. As used herein, "carbon steels" are those steels having no specified minimum quantity for any alloying element (other than the commonly accepted amounts of manganese, silicon and copper) and containing only an incidental amount of any element other than carbon, silicon, manganese, copper, sulfur and phosphorus. As used herein, "mild steels" are those carbon steels with a maximum of about 0.25 wt. % carbon. As used herein, "alloy steels" are those steels containing specified quantities of alloying elements (other than carbon and the commonly accepted amounts of manganese, copper, silicon, sulfur and phosphorus) within the limits recognized for constructional alloy steels, added to effect changes in mechanical or physical properties. Alloy steels will contain less than about 10 wt. % chromium. As used herein, "stainless steels" are any of several steels containing at least about 10 wt. %, alternatively about 12 wt. % to about 30 wt. %, chromium as the principal alloying element. As used herein, "austenitic stainless steels" are those having an austenitic microstructure. These steels are known in the art. Examples include 300 series stainless steels such as 304, 310, 316, 321, and 347. Austenitic stainless steels typically contain between about 16 wt. % and about 20 wt. % chromium and between about 8 wt. % and about 15 wt. % nickel. Steels with less than about 5 wt. % nickel are less susceptible to halide stress corrosion cracking. Suitable substrates may comprise one or more of the foregoing metallurgies.

Generally, groups of elements are indicated using the numbering scheme indicated in the version of the periodic table of elements published in *Chemical and Engineering News*, 63(5), 27, 1985. In some instances, a group of elements may be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure (general or specific) presented is intended to encompass all conformational isomers, regioisomers, stereoisomers, and mixtures thereof that may arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to hexane includes n-hexane, 2-methyl-pentane, 3-methyl-pentane, 2,2-dimethyl-butane, and 2,3-dimethyl-butane; and a general reference to a butyl group includes a n-butyl group, a sec-butyl group, an iso-butyl group, and a t-butyl group.

In one aspect, a chemical "group" may be defined or described according to how that group is formally derived from a reference or "parent" compound, for example, by the number of hydrogen atoms removed from the parent compound to generate the group, even if that group is not literally synthesized in such a manner. These groups may be utilized as substituents or coordinated or bonded to metal atoms. By way of example, an "alkyl group" formally may be derived by removing one hydrogen atom from an alkane. The disclosure that a substituent, ligand, or other chemical moiety may constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

Various numerical ranges are disclosed herein. When a range of any type is disclosed or claimed herein, the intent is to disclose or claim individually each possible number that such a range could reasonably encompass, including end points of the range as well as any sub-ranges and combinations of sub-ranges encompassed therein, unless otherwise specified. As a representative example, the present application discloses that the methods provided herein may use or produce a catalyst containing Cl and F at a molar ratio of Cl:F in a range from about 0.5:1 to about 4:1 in certain aspects. By a disclosure that the molar ratio of Cl:F may be in a range from about 0.5:1 to about 4:1, the intent is to recite that the molar ratio may be any molar ratio within the range and, for example, may be equal to about 0.5:1, about 0.6:1, about 0.7:1, about 0.8:1, about 0.9:1, about 1:1, about 2:1, about 3:1, or about 4:1. Additionally, the molar ratio of Cl:F may be within any range from about 0.5:1 to about 4:1 (for example, the molar ratio may be in a range from about 0.5:1 to about 2:1), and this also includes any combination of ranges between about 0.5:1 and about 4:1. Likewise, all other ranges disclosed herein should be interpreted in a manner similar to this example.

The term "about" means that amounts, sizes, formulations, parameters, and other quantities and characteristics are not and need not be exact, but may be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, preferably within 5% of the reported numerical value.

As used herein, the term "hydrocarbon" refers to a compound containing only carbon and hydrogen atoms. Other identifiers may be utilized to indicate the presence of particular groups, if any, in the hydrocarbon (e.g., halogenated hydrocarbon indicates that the presence of one or more halogen atoms replacing an equivalent number of hydrogen atoms in the hydrocarbon).

An "aromatic" compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds, e.g., benzene, toluene, and xylenes) and "heteroarenes" (heteroaromatic compounds formally derived from arenes by replacement of one or more methine (—C═) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2)). As disclosed herein, the term "substituted" may be used to describe an aromatic group, arene, or heteroarene, wherein a non-hydrogen moiety formally replaces a hydrogen atom in the compound, and is intended to be non-limiting, unless specified otherwise.

As used herein, the term "alkane" refers to a saturated hydrocarbon compound. Other identifiers may be utilized to indicate the presence of particular groups, if any, in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. The alkane or alkyl group may be linear or branched unless otherwise specified.

A "cycloalkane" is a saturated cyclic hydrocarbon, with or without side chains, for example, cyclobutane, cyclopentane, cyclohexane, methyl cyclopentane, and methyl cyclohexane. Other identifiers may be utilized to indicate the presence of particular groups, if any, in the cycloalkane (e.g., halogenated cycloalkane indicates that the presence of one or more halogen atoms replacing an equivalent number of hydrogen atoms in the cycloalkane).

The term "halogen" has its usual meaning. Examples of halogens include fluorine, chlorine, bromine, and iodine.

The term "contacting" is used herein to describe methods, processes, and compositions wherein the components are contacted or combined together in any order, in any manner, and for any length of time, unless otherwise specified. For example, the components may be contacted by blending or mixing. Further, unless otherwise specified, the contacting of any component may occur in the presence or absence of any other component of the methods, processes, and compositions described herein. Combining additional materials or components may be done by any suitable technique. Further, "contacting" two or more components may result in a solution, a slurry, a mixture, a reaction mixture, or a reaction product.

Molar selectivities are defined as:

$$\text{Benzene selectivity: } S_{Bz} = \frac{\dot{n}_{Bz,prod}}{\dot{n}_{convC6,feed} - \dot{n}_{convC6,prod}} \quad \text{Eq. 1}$$

$$\text{Toluene selectivity: } S_{Tol} = \frac{\dot{n}_{Tol,prod}}{\dot{n}_{convC7,feed} - \dot{n}_{convC7,prod}} \quad \text{Eq. 2}$$

$$\text{Benzene + Toluene selectivity: } S_{Bz+Tol} = \frac{\dot{n}_{Bz,prod} + \dot{n}_{Tol,prod}}{\dot{n}_{convC6,C7,feed} - \dot{n}_{convC6,C7,prod}} \quad \text{Eq. 3}$$

$$\text{Aromatics selectivity: } S_{arom} = \frac{\dot{n}_{Bz,prod} + \dot{n}_{Tol,prod} + \dot{n}_{C8+arom,prod}}{\dot{n}_{convC6-C8+,feed} - \dot{n}_{convC6-C8+,prod}} \quad \text{Eq. 4}$$

Conversion is defined as the number of moles converted per mol of "convertible" hydrocarbons fed:

$$\text{C6 conversion: } X_{C6} = \frac{\dot{n}_{convC6,feed} - \dot{n}_{convC6,prod}}{\dot{n}_{convC6,feed}} \quad \text{Eq. 5}$$

$$\text{C7 conversion: } X_{C7} = \frac{\dot{n}_{convC7,feed} - \dot{n}_{convC7,prod}}{\dot{n}_{convC7,feed}} \quad \text{Eq. 6}$$

$$\text{C6 + C7 conversion: } X_{C6+C7} = \frac{\dot{n}_{convC6,feed} + \dot{n}_{convC7,feed} - \dot{n}_{convC6,prod} - \dot{n}_{convC7,prod}}{\dot{n}_{convC6,feed} + \dot{n}_{convC7,feed}} \quad \text{Eq. 7}$$

In these equations, $\dot{n}$ indicates a molar flow rate in a continuous reactor or the number of moles in a batch reactor.

As used herein, the term "convertible hydrocarbon," "convertible $C_6$ species," or "convertible $C_7$ species" refers to a hydrocarbon compound which is readily reacted to form aromatic hydrocarbons under aromatization process conditions. A "non-convertible hydrocarbon" is a highly-branched hydrocarbon that is not readily reacted to form aromatic hydrocarbons under aromatization process conditions. A "non-convertible hydrocarbon" may comprise highly-branched hydrocarbons having six or seven carbon atoms with an internal quaternary carbon, or hydrocarbons having six carbons atoms and two adjacent internal tertiary carbons, or mixtures thereof. A "convertible $C_6$ species" is a hydrocarbon containing six carbons without an internal quaternary carbon or two adjacent internal tertiary carbons, for example, n-hexane, 2-methyl-pentane, 3-methyl-pentane, cyclohexane, and methyl cyclopentane. A "convertible $C_7$ species" is a hydrocarbon containing seven carbons without an internal quaternary carbon, for example, n-heptane, 2-methyl-hexane, 3-methyl-hexane, 2,3-dimethyl-pentane, 2,4-dimethyl-pentane, methyl cyclohexane, and dimethyl cyclopentane. The highly branched hydrocarbons with six or seven carbon atoms and an internal quaternary carbon may comprise, for example, 2,2-dimethylbutane, 2,2-dimethyl-pentane, 3,3-dimethylpentane, and 2,2,3-trimethylbutane. The highly branched hydrocarbons with six carbon atoms and an adjacent internal tertiary carbon may comprise, for example, 2,3-dimethylbutane. The non-convertible highly branched hydrocarbons do not easily convert to aromatic products, and instead tend to convert to light hydrocarbons under aromatization process conditions.

Although any methods and materials similar or equivalent to those described herein may be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are methods for regenerating a spent catalyst, such as a spent aromatization catalyst, in a metal reactor. Related reforming processes also are disclosed. Beneficially, as compared to other methods of regenerating a spent catalyst, the methods described herein—e.g., a chlorination step before a decoking or carbon burn step, and a fluorination step after the decoking or carbon burn step—result in a regenerated catalyst with unexpectedly improved catalyst activity and selectivity, and reduced corrosivity in conventional metal or stainless steel reactors.

While not wishing to be bound by the following theory, it is believed that methods of regenerating a spent catalyst using a non-metal reactor (e.g., glass or quartz) overlook the fact that commercial processing of spent catalysts requires a metal reactor, such as a stainless steel reactor. A particular technique for regenerating a spent catalyst may appear successful when employed in a quartz reactor, but the overall impact of chlorine, fluorine, oxygen, and/or moisture at elevated temperatures may lead to catastrophic corrosion when that same technique is employed in a metal reactor. Additionally, the activity and selectivity performance of the regenerated catalyst may be negatively impacted after processing in a metal reactor, whereas the same impact is not found when using quartz or other non-metal reactors typical found in controlled laboratory environments.

Methods for Regenerating Spent Catalysts

Various methods for regenerating spent catalysts comprising a transition metal and a catalyst support in a metal reactor are disclosed and described. One such method of regenerating a spent catalyst in a metal reactor may comprise (or consist essentially of, or consist of):

(1) contacting the spent catalyst with a chlorine-containing stream comprising a chlorine-containing compound to produce a chlorinated spent catalyst;

(2) contacting the chlorinated spent catalyst with a decoking gas stream comprising oxygen to produce a de-coked catalyst; and (3) contacting the de-coked catalyst with a fluorine-containing stream comprising a fluorine-containing compound.

Generally, the features of any of the methods disclosed herein (e.g., the metal reactor, the spent catalyst, the transition metal, the catalyst support, the fluorine-containing stream, the chlorine-containing stream, the conditions under which the fluorination step is conducted, the conditions under which the chlorination step is conducted, the decoking gas stream, the conditions under which the decoking step is conducted, among others) are independently described herein, and these features may be combined in any combination to further describe the disclosed methods. Moreover, other process steps may be conducted before, during, and/or after any of the steps listed in the disclosed methods, unless stated otherwise. Additionally, regenerated catalysts or reactivated catalysts produced in accordance with any of the disclosed methods/processes are within the scope of this disclosure and are encompassed herein.

The steps of these methods that utilize a fluorine-containing stream often may be referred to as fluorination steps, while the steps of these methods that utilize a chlorine-containing stream often may be referred to as chlorination steps. Any compositional attributes of the fluorine-containing stream and the chlorine-containing stream are meant to refer to the respective incoming fluorine-containing stream and chlorine-containing stream, prior to contacting the catalyst, unless expressly stated otherwise. As one of skill in the art would readily recognize, the outgoing fluorine-containing stream and chlorine-containing stream, after contacting the catalyst and the metal reactor, may vary significantly in composition from the respective incoming fluorine-containing stream and chlorine-containing stream.

Referring now to step (1), the chlorine-containing compound in the chlorine-containing stream may be any suitable chlorine-containing compound or any chlorine-containing compound disclosed herein. For instance, illustrative chlorine-containing compounds may include, but are not limited to, hydrochloric acid, chlorine gas ($Cl_2$), carbon tetrachloride, tetrachloroethylene, chlorobenzene, methyl chloride, methylene chloride, chloroform, allyl chloride, trichloroethylene, a chloramine, a chlorine oxide, a chlorine acid, chlorine dioxide, dichlorine monoxide, dichlorine heptoxide, chloric acid, perchloric acid, ammonium chloride, tetramethylammonium chloride, tetraethyl ammonium chloride, tetrapropylammonium chloride, tetrabutylammonium chloride, methyltriethylammonium chloride, and the like, or any combination thereof. Other suitable chlorine-containing compounds may include arenes and alkyl-substituted arenes (e.g., benzene, toluene, and xylenes) where at least one hydrogen atom is replaced with a Cl atom.

In some aspects, the chlorine-containing compound may comprise (or consist essentially of, or consist of) hydrochloric acid; alternatively, chlorine gas ($Cl_2$); alternatively, carbon tetrachloride; alternatively, tetrachloroethylene; alternatively, chlorobenzene; alternatively, methyl chloride; alternatively, methylene chloride; alternatively, chloroform; alternatively, allyl chloride; alternatively, trichloroethylene; alternatively, a chloramine; alternatively, a chlorine oxide; alternatively, a chlorine acid; alternatively, chlorine dioxide; alternatively, dichlorine monoxide; alternatively, dichlorine heptoxide; alternatively, chloric acid; alternatively, perchloric acid; alternatively, ammonium chloride; alternatively, tetramethylammonium chloride; alternatively, tetraethylammonium chloride; alternatively, tetrapropylammonium chloride; alternatively, tetrabutylammonium chloride; or alternatively, methyltriethylammonium chloride.

In other aspects, the chlorine-containing compound may comprise (or consist essentially of, or consist of) chlorine gas ($Cl_2$). In addition to the chlorine-containing compound, the chlorine-containing stream may further comprise an inert gas, such as helium, neon, argon, nitrogen, or combinations of two or more of these materials. In certain aspects, the chlorine-containing stream may comprise (or consist essentially of, or consist of) a chlorine-containing compound and an inert gas, and the inert gas may be or may comprise nitrogen. In a further aspect, the chlorine-containing stream may comprise (or consist essentially of, or consist of) chlorine gas ($Cl_2$) and nitrogen.

While not being limited thereto, the amount of chlorine (Cl) in the chlorine-containing stream often may be less than about 15% by volume. For instance, the chlorine-containing stream may comprise an amount of the chlorine-containing compound that is controlled to give a concentration in ppmv (ppm by volume) of Cl in the chlorine-containing stream of less than about 100,000; alternatively, a ppmv of Cl of less than about 50,000; alternatively, a ppmv of Cl of less than about 25,000; alternatively, a ppmv of Cl of less than about 10,000. Suitable ranges for the concentration of Cl may include, but are not limited to, the following ranges: from about 50 to about 100,000 ppmv, from about 50 to about 50,000 ppmv, from about 50 to about 25,000 ppmv, from about 100 to about 20,000 ppmv, from about 250 to about 25,000 ppmv, from about 500 to about 25,000 ppmv, from about 1,000 to about 25,000 ppmv, from about 5,000 to about 50,000 ppmv, from about 2,500 to about 35,000 ppmv, or from about 7,500 to about 35,000 ppmv, and the like.

The chlorine-containing stream may be substantially free of an oxygen-containing compound (e.g., oxygen ($O_2$) and water ($H_2O$)), i.e., may contain less than 100 ppmw (ppm by weight) of an oxygen-containing compound. Therefore, it is contemplated that the amount of any oxygen-containing compound in the chlorine-containing stream may be less than 50 ppmw, less than 25 ppmw, less than 10 ppmw, less than 5 ppmw, or less than 3 ppmw, in certain aspects. In other aspects, the amount of any oxygen-containing compound in the chlorine-containing stream may be in range from about 0.1 to 100 ppmw, from about 0.5 to 100 ppmw, from about 1 to 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, it is believed that it may be beneficial to have substantially no oxygen added during the chlorination step of the method of regenerating a spent catalyst. Moreover, although not required, the chlorine-containing stream may be substantially free of fluorine-containing compounds, i.e., may contain less than 100 ppmw (ppm by weight) of fluorine-containing compounds. As above, it is contemplated that the amount of fluorine-containing compounds in the chlorine-containing stream may be, for instance, less than 50 ppmw, less than 10 ppmw, in a range from about 0.1 to 100 ppmw, in a range from about 0.1 to about 50 ppmw, or in a range from about 0.1 to about 10 ppmw, and the like.

The chlorination step may be conducted at a variety of temperatures and time periods. For instance, the chlorination step may be conducted at a chlorination temperature in a range from about 0° C. to about 500° C.; alternatively, from about 0° C. to about 300° C.; alternatively, from about 20° C. to about 400° C.; alternatively, from about 20° C. to about 300° C.; alternatively, from about 30° C. to about 300° C.; alternatively, from about 40° C. to about 300° C.; alternatively, from about 100° C. to about 250° C.; alternatively, from about 150° C. to about 300° C.; alternatively, from about 200° C. to about 300° C.; alternatively, or alternatively, from about 150° C. to about 275° C. In these and other aspects, these temperature ranges also are meant to encompass circumstances where the chlorination step is conducted at a series of different temperatures, instead of at a single fixed temperature, falling within the respective ranges.

The duration of the chlorination step is not limited to any particular period of time. Hence, the chlorination step may be conducted, for example, in a time period ranging from as little as 30-45 minutes to as long as 12-24 hours, 36-48 hours, or more. The appropriate chlorination time may depend upon, for example, the chlorination temperature and the amount of chlorine in the chlorine-containing stream, among other variables. Generally, however, the chlorination step may be conducted in a time period that may be in a range from about 45 minutes to about 48 hours, such as, for example, from about 1 hour to about 48 hours, from about 45 minutes to about 24 hours, from about 45 minutes to about 18 hours, from about 1 hour to about 12 hours, from about 2 hours to about 12 hours, from about 4 hours to about 10 hours, or from about 2 hours to about 8 hours.

Step (2) of the method for regenerating a spent catalyst often may be referred to as the carbon burn step, or decoking step, and in this step, a chlorinated spent catalyst may be contacted with a decoking gas stream comprising oxygen. In addition to oxygen, the decoking gas stream may comprise an inert gas, i.e., the decoking gas stream may comprise (or consist essentially of, or consist of) oxygen and an inert gas. Typical inert gasses useful in the carbon burn step may encompass helium, neon, argon, nitrogen, and the like, and this includes combinations of two or more of these materials. In certain aspects, the decoking gas stream may comprise (or consist essentially of, or consist of) oxygen and nitrogen; alternatively, air and nitrogen; or alternatively, air.

Since the decoking gas stream may comprise air, the decoking gas stream may comprise about 20-21 mole % oxygen. More often, however, the amount of oxygen in the decoking gas stream may be less than about 10 mole %. For example, in some aspects, the decoking gas stream may comprise less than about 8 mole %, less than about 5 mole %, or less than about 3 mole % oxygen. Accordingly, suitable ranges for the mole % of oxygen in the decoking gas stream may include, but are not limited to, the following ranges: from about 0.1 to about 25 mole %, from about 0.1 to about 20 mole %, from about 0.1 to about 10 mole %, from about 0.2 to about 10 mole %, from about 0.2 to about 5 mole %, from about 0.3 to about 5 mole %, from about 0.5 to about 5 mole %, from about 0.5 to about 4 mole %, from about 0.5 to about 3 mole %, or from about 1 to about 3 mole %, and the like.

In an aspect, the decoking gas stream may be substantially halogen-free, i.e., substantially free of halogen-containing compounds. In this context, "substantially halogen-free" means less than 100 ppmw (ppm by weight) of halogen-containing compounds, such as chlorine-containing compounds, in the decoking gas stream. Therefore, it is contemplated that the amount of halogen-containing compounds in the decoking gas stream may be less than 50 ppmw, less than 40 ppmw, less than 25 ppmw, less than 10 ppmw, less than 5 ppmw, or less than 3 ppmw, in certain aspects. In other aspects, the amount of halogen-containing compounds in the decoking gas stream may be in range from about 0.1 to about 100 ppmw, from about 0.5 to 100 ppmw, from about 1 to 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, it is believed that it may be beneficial to have substantially no halogens, such as chlorine, added during the carbon burn step of the method of regenerating a spent catalyst.

In another aspect, the decoking gas stream may be substantially free of water, and in this regard, "substantially free" means less than 100 ppmw (ppm by weight) of water in the decoking gas stream. Therefore, it is contemplated that the amount of water in the decoking gas stream may be less than 50 ppmw, less than 25 ppmw, less than 10 ppmw, less than 5 ppmw, or less than 3 ppmw, in certain aspects. In other aspects, the amount of water in the decoking gas stream may be in range from about 0.1 to 100 ppmw, from about 0.5 to 100 ppmw, from about 1 to 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, it is believed that it may be beneficial to have substantially no water added during the carbon burn step of the method of regenerating a spent catalyst.

Similar to that described above for the chlorine-containing stream, any compositional attributes of the decoking gas stream are meant to refer to the incoming decoking gas stream, prior to contacting the chlorinated spent catalyst and the metal reactor, unless expressly stated otherwise. As one of skill in the art would readily recognize, the outgoing decoking gas stream, after contacting the chlorinated spent catalyst, may vary significantly in composition from the incoming decoking gas stream. For instance, chlorine deposited during the chlorination may elute, in some circumstances, from the catalyst during the carbon burn step. Moreover, water may be produced during the carbon burn step, and thus, water may be detected in the outgoing decoking gas stream.

The carbon burn step may be conducted at a variety of temperatures and time periods. For instance, the carbon burn step may be conducted at a peak decoking temperature in a range from about 150° C. to about 600° C.; alternatively, from about 200° C. to about 500° C.; alternatively, from about 300° C. to about 600° C.; alternatively, from about 300° C. to about 550° C.; alternatively, from about 300° C. to about 500° C.; alternatively, from about 320° C. to about 480° C.; alternatively, from about 340° C. to about 460° C.; or alternatively, from about 350° C. to about 450° C. In these and other aspects, these temperature ranges also are meant to encompass circumstances where the carbon burn step is conducted at a series of different temperatures (e.g., an initial decoking temperature, a peak decoking temperature), instead of at a single fixed temperature, falling within the respective ranges. For instance, and not limited thereto, the carbon burn step may start at an initial decoking temperature which is the same as a chlorine purging temperature (discussed further herein below). Thus, for example, the carbon burn step may commence at an initial decoking temperature in a range from about 0° C. to about 300° C., from about 20° C. to about 250° C., from about 50° C. to about 200° C., or from about 150° C. to about 260° C. Subsequently, the temperature of the carbon burn step may be increased to a peak decoking temperature, for example, in a range from about 300° C. to about 600° C., or from about 350° C. to about 450° C.

The duration of the carbon burn step is not limited to any particular period of time. Hence, the carbon burn step may be conducted, for example, in a time period ranging from as little as 30-45 minutes to as long as 48-72 hours, or more. The appropriate decoking time may depend upon, for example, the initial decoking temperature, the peak decoking temperature and the amount of oxygen in the decoking gas stream, among other variables. Generally, however, the carbon burn step may be conducted in a time period that may be in a range from about 45 minutes to about 72 hours, such as, for example, from about 1 hour to about 72 hours, from about 24 hours to about 72 hours, from about 12 hours to about 60 hours, from about 12 hours to about 48 hours, or from about 1 hour to about 6 hours.

Alternatively, the carbon burn step may be conducted for a time period sufficient to reduce the wt. % of carbon on the chlorinated spent catalyst to less than about 1 wt. % (a de-coked catalyst). In some aspects, the carbon burn step may be conducted for a time period sufficient to reduce the wt. % of carbon on the chlorinated spent catalyst to less than about 0.75 wt. %, less than about 0.5 wt. %, or less than about 0.2 wt. %. In other aspects, the carbon burn step may be conducted for a time period determined by monitoring the $CO_2$ level in the outgoing or exiting decoking gas stream, after contacting the catalyst. Hence, the carbon burn step may be conducted for a time period sufficient to reduce the amount of $CO_2$ in the outgoing or exiting decoking gas stream, after contacting the catalyst, to less than about 100 ppmv, for example, less than about 50 ppmv, or less than about 20 ppmv.

Alternatively, the carbon burn step may be conducted for a time period sufficient to result in a regenerated catalyst having an activity that is from about 50% to about 80% of the activity of the fresh catalyst, for example, from about 50% to about 75%, or from about 55% to about 75%. In this regard, the activity of the regenerated catalyst is based on returning to within about 50%-80% of the fresh catalyst activity of the same production run of catalyst, tested on the same equipment and under the same method and conditions.

In step (3) of the method for regenerating a spent catalyst, the de-coked catalyst may be contacted with a fluorine-containing stream comprising a fluorine-containing compound. Suitable fluorine-containing compounds may include, but are not limited to, hydrofluoric acid, fluorine gas ($F_2$), 2,2,2-trifluoroethanol, tetrafluoroethylene, carbon tetrafluoride, carbon trifluoride, fluoromethane, heptafluoropropane, decafluorobutane, hexafluoroisopropanol, tetrafluoropropanol, pentafluoropropanol, hexafluorophenylpropanol, perfluorobutyl alcohol, hexafluor-2-propanol, pentafluoro-1-propanol, tetrafluoro-1-propanol, 1,1,1,3,3,3-hexafluoro-2-propanol, 2,2,3,3,3-pentafluoro-1-propanol, ammonium fluoride, tetramethylammonium fluoride, tetraethylammonium fluoride, tetrapropylammonium fluoride, tetrabutylammonium fluoride, methyltriethylammonium fluoride, and the like, or any combination thereof. Other suitable fluorine-containing compounds may include arenes and alkyl-substituted arenes (e.g., benzene, toluene, and xylenes) where at least one hydrogen atom is replaced with a F atom.

In another aspect, the fluorine-containing compound may comprise (or consist essentially of, or consist of) hydrofluoric acid; alternatively, fluorine gas ($F_2$); alternatively, 2,2,2-trifluoroethanol; alternatively, tetrafluoroethylene; alternatively, carbon tetrafluoride; alternatively, carbon trifluoride; alternatively, fluoromethane; alternatively, heptafluoropropane; alternatively, decafluorobutane; alternatively, hexafluoroisopropanol; alternatively, tetrafluoropropanol; alternatively, pentafluoropropanol; alternatively, hexafluorophenylpropanol; alternatively, perfluorobutyl alcohol; alternatively, hexafluor-2-propanol; alternatively, pentafluoro-1-propanol; alternatively, tetrafluoro-1-propanol; alternatively, 1,1,1,3,3,3-hexafluoro-2-propanol; alternatively, 2,2,3,3,3-pentafluoro-1-propanol; alternatively, ammonium fluoride; alternatively, tetramethylammonium fluoride; alternatively, tetraethylammonium fluoride; alternatively, tetrapropylammonium fluoride; alternatively, tetrabutylammonium fluoride; or alternatively, methyltriethylammonium fluoride.

In another aspect, the fluorine-containing compound may comprise (or consist essentially of, or consist of) fluorine gas ($F_2$). In addition to fluorine, the fluorine-containing stream may further comprise an inert gas, such as helium, neon, argon, nitrogen, or combinations of two or more of these materials. In yet another aspect, the fluorine-containing stream may comprise (or consist essentially of, or consist of) a fluorine-containing compound and an inert gas, and the inert gas may be or may comprise nitrogen. In still another aspect, the fluorine-containing stream may comprise (or consist essentially of, or consist of) fluorine gas ($F_2$) and nitrogen.

While not being limited thereto, the amount of fluorine (F) in the fluorine-containing stream often may be less than about 15% by volume. For instance, the fluorine-containing stream may comprise an amount of the fluorine-containing compound that is controlled to give a concentration in ppmv (ppm by volume) of F in the fluorine-containing stream of less than about 100,000; alternatively, a ppmv of F of less than about 50,000; alternatively, a ppmv of F of less than about 25,000; alternatively, a ppmv of F of less than about 10,000. Suitable ranges for the concentration of F may include, but are not limited to, the following ranges: from about 50 to about 150,000 ppmv, from about 50 to about 100,000 ppmv, from about 1,000 to about 15,000 ppmv, from about 50 to about 5,000 ppmv, from about 100 to about 20,000 ppmv, from about 250 to about 25,000 ppmv, from about 5,000 to about 50,000 ppmv, from about 1,000 to about 25,000 ppmv, from about 5,000 to about 25,000 ppmv, from about 2,500 to about 35,000 ppmv, or from about 7,500 to about 35,000 ppmv, and the like.

The fluorine-containing stream may be substantially free of oxygen-containing compounds (e.g., oxygen ($O_2$) and water ($H_2O$)), i.e., may contain less than 100 ppmw (ppm by weight) of oxygen-containing compounds. Therefore, it is contemplated that the amount of oxygen-containing compounds in the fluorine-containing stream may be less than 50 ppmw, less than 25 ppmw, less than 10 ppmw, less than 5 ppmw, or less than 3 ppmw, in certain aspects. In other aspects, the amount of oxygen-containing compounds in the fluorine-containing stream may be in range from about 0.1 to 100 ppmw, from about 0.5 to 100 ppmw, from about 1 to 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, it is believed that it may be beneficial to have substantially no oxygen added during the fluorination step of the method of regenerating a spent catalyst. Moreover, although not required, the fluorine-containing stream may be substantially free of chlorine-containing compounds, i.e., may contain less than 100 ppmw (ppm by weight) of chlorine-containing compounds. As above, it is contemplated that the amount of chlorine-containing compounds in the fluorine-containing stream may be, for instance, less than 50 ppmw, less than 10 ppmw, in a range from about 0.1 to 100 ppmw, in a range from about 0.1 to about 50 ppmw, or in a range from about 0.1 to about 10 ppmw, and the like.

The fluorination step may be conducted at a variety of temperatures and time periods. For instance, the fluorination step may be conducted at a fluorination temperature in a range from about 0° C. to about 500° C.; alternatively, from about 0° C. to about 300° C.; alternatively, from about 20° C. to about 300° C.; alternatively, from about 20° C. to about 250° C.; alternatively, from about 20° C. to about 150° C.; alternatively, from about 35° C. to about 300° C.; alternatively, from about 35° C. to about 200° C.; alternatively, from about 50° C. to about 250° C.; alternatively, from about 50° C. to about 200° C.; alternatively, from about 100° C. to about 300° C.; alternatively, from about 100° C. to about 250° C.; alternatively, from about 150° C. to about 275° C.; or alternatively, from about 15° C. to about 50° C. In these and other aspects, these temperature ranges also are meant to encompass circumstances where the fluorination step is conducted at a series of different temperatures, instead of at a single fixed temperature, falling within the respective ranges.

The duration of the fluorination step is not limited to any particular period of time. Hence, the fluorination step may be conducted, for example, in a time period ranging from as little as 30-45 minutes to as long as 12-24 hours, 36-48 hours, or more. The appropriate fluorination time may depend upon, for example, the fluorination temperature and the amount of fluorine in the fluorine-containing stream, among other variables. Generally, however, the fluorination step may be conducted in a time period that may be in a range from about 45 minutes to about 48 hours, such as, for example, from about 1 hour to about 48 hours, from about 45 minutes to about 24 hours, from about 45 minutes to about 18 hours, from about 1 hour to about 12 hours, from about 2 hours to about 12 hours, from about 4 hours to about 10 hours, or from about 2 hours to about 8 hours.

In various aspects contemplated herein, the methods of regenerating a spent catalyst may further include one or more optional steps performed prior to the chlorination step and the carbon burn step. For example, a method of regenerating a spent catalyst may further comprise a partial decoking step prior to the chlorination step, and/or may further comprise a pre-drying step prior to the chlorination step. These optional pre-chlorination steps are discussed in greater detail herein below. In one aspect, at least one of these optional steps may be performed in a method of regenerating a spent catalyst, while in another aspect, both of these optional steps may be performed. The pre-chlorination steps may be performed in any order, however, in a particular aspect, the partial decoking step may be performed first, followed by the pre-drying step.

In an aspect, a method of regenerating a spent catalyst (e.g., comprising a transition metal and a catalyst support) comprising a chlorination step, followed by a carbon burn step, and then by a fluorination step, may further comprise a partial decoking step prior to the chlorination step. This partial decoking step generally may comprise contacting the spent catalyst with a partial decoking gas stream comprising oxygen.

The composition of the partial decoking gas stream may encompass the same potential attributes as that described above for the decoking gas stream employed in the carbon burn step. Thus, in addition to oxygen, the partial decoking gas stream may comprise an inert gas, such as helium, neon, argon, nitrogen, or combinations of two or more of these materials. In an aspect, the partial decoking gas stream may comprise (or consist essentially of, or consist of) oxygen and nitrogen; alternatively, air and nitrogen; or alternatively, air. In another aspect, the partial decoking gas stream often may comprise, for example, from about 0.1 to about 25 mole % oxygen, from about 0.1 to about 20 mole % oxygen, from about 0.2 to about 10 mole % oxygen, from about 0.2 to about 5 mole % oxygen, from about 0.3 to about 5 mole % oxygen, from about 0.5 to about 5 mole % oxygen, from about 0.5 to about 4 mole % oxygen, from about 0.5 to about 3 mole % oxygen, or from about 1 to about 3 mole % oxygen, and the like. In yet another aspect, the partial decoking gas stream may be substantially halogen-free or substantially free of halogen-containing compounds, i.e., having less than 100 ppmw (ppm by weight) of halogen-containing compounds in the partial decoking gas stream, such as, for example, less than 50 ppmw, less than 25 ppmw, less than 10 ppmw, less than 5 ppmw, or less than 3 ppmw, of halogen-containing compounds in the partial decoking gas stream. In still another aspect, the partial decoking gas stream may be substantially free of water, i.e., having less than 100 ppmw of water in the partial decoking gas stream, such as, for example, less than 50 ppmw, less than 25 ppmw, less than 10 ppmw, less than 5 ppmw, or less than 3 ppmw, of water in the partial decoking gas stream.

The partial decoking step differs from the carbon burn step in that it may be conducted at a much lower temperature. Generally, the partial decoking step may be conducted at a partial decoking temperature in a range from about 125° C. to about 260° C.; alternatively, from about 125° C. to about 250° C.; alternatively, from about 150° C. to about 250° C.; alternatively, from about 175° C. to about 250° C.; alternatively, from about 150° C. to about 225° C.; or alternatively, from about 175° C. to about 225° C. In these and other aspects, these temperature ranges also are meant to encompass circumstances where the partial decoking step is conducted at a series of different temperatures, instead of at a single fixed temperature, falling within the respective ranges.

The duration of the partial decoking step is not limited to any particular period of time. Typically, the partial decoking step may be conducted in a time period ranging from as little as 30-45 minutes to as long as 48 hours (or more), but more typically, the partial decoking step may be conducted in a time period that may be in a range from about 1 hour to about 36 hours, such as, for example, from about 2 hours to about 36 hours, from about 1 hour to about 24 hours, from about 1 hour to about 18 hours, or from about 2 hours to about 24 hours.

Alternatively, the partial decoking step may be conducted for a time period sufficient to reduce the wt. % of carbon on the spent catalyst to within a range from about 1 to about 10 wt. %, such as, for example, from about 2 to about 10 wt. %, from about 2 to about 8 wt. %, from about 1 to about 7 wt. %, from about 3 to about 6 wt. %, or from about 4 to about 5 wt. % carbon. While not wishing to be bound by theory, it is believed that operational health and safety benefits may be achieved by removing liquid hydrocarbons and light oligomers prior to opening an aromatization reactor, or storing or shipping the spent catalyst for off-site regeneration.

In an aspect, a method of regenerating a spent catalyst (e.g., comprising a transition metal and a catalyst support) comprising a chlorination step, followed by a carbon burn step, and then by a fluorination step, may further comprise a pre-drying step prior to the chlorination step. This pre-drying step generally may comprise contacting the spent catalyst with a pre-drying gas stream comprising (or consisting essentially of, or consisting of) an inert gas. The inert gas may be helium, neon, argon, nitrogen, or combinations of two or more of these materials; alternatively, helium; alternatively, neon; alternatively, argon; or alternatively, nitrogen. Additionally, in some aspects, the pre-drying gas stream may be substantially free of oxygen-containing compounds (e.g., oxygen or water), as discussed above in relation to the chlorination step. Hence, the pre-drying step may be conducted in the presence of less than 100 ppmw of oxygen-containing compounds, or less than 50 ppmw, or less than 25 ppmw, or less than 10 ppmw, or less than 5 ppmw, or less than 3 ppmw.

The pre-drying step may be performed at a pre-drying temperature which generally may encompass the same temperature range as the chlorination temperature used in the chlorination step. Accordingly, the pre-drying temperature may be in a range from about 0° C. to about 500° C.; alternatively, from about 0° C. to about 400° C.; alternatively, from about 20° C. to about 300° C.; alternatively, from about 20° C. to about 250° C.; alternatively, from about 20° C. to about 150° C.; alternatively, from about 35° C. to about 300° C.; alternatively, from about 35° C. to about 200° C.; alternatively, from about 50° C. to about 250° C.; alternatively, from about 50° C. to about 200° C.; alternatively, from about 100° C. to about 500° C.; alternatively, from about 100° C. to about 250° C.; or alternatively, from about 180° C. to about 280° C. In these and other aspects, these temperature ranges also are meant to encompass circumstances where the pre-drying step is conducted at a series of different temperatures, instead of at a single fixed temperature, falling within the respective ranges.

The duration of the pre-drying step is not limited to any particular period of time. Typically, the pre-drying step may be conducted in a time period ranging from as little as 30-45 minutes to as long as 48-72 hours (or more), but more typically, the pre-drying step may be conducted in a time period that may be in a range from about 1 hour to about 72 hours, such as, for example, from about 1 hour to about 48 hours, from about 1 hour to about 36 hours, from about 2 hours to about 24 hours, or from about 2 hours to about 18 hours.

Alternatively, the pre-drying step may be conducted for a time period sufficient to reduce the moisture content of the spent catalyst to less than about 4 wt. %, less than about 2 wt. %, less than about 1 wt. %, less than about 0.5 wt. %, or less than about 0.1 wt. %. While not wishing to be bound by theory, it is believed that it may be beneficial to have substantially no moisture present when the chlorination step is begun to reduce corrosivity of the chlorine-containing stream on the reactor metallurgy. For instance, dry halogens and dry halogen acids are not corrosive and may be in employed in carbon steel environments, however, once moisture is present, even stainless steel may not be sufficient, and high alloy steels may be required.

In various aspects contemplated herein, the methods of regenerating a spent catalyst may further include one or more optional intermediate steps performed after the chlorination step, but prior to the carbon burn step. For example, a method of regenerating a spent catalyst may further comprise a chlorine purging step prior to the carbon burn step and/or may further comprise a hydrocarbon treatment step prior to the carbon burn step. These optional intermediate steps are discussed in greater detail herein below. In one aspect, at least one of these optional intermediate steps may be performed in a method of regenerating a spent catalyst, while in another aspect, both of these optional intermediate steps may be performed. When both intermediate steps are performed, the intermediate steps may be performed in any order, for example, the chlorination step, followed by the hydrocarbon treatment step, then the chlorine purging step, and then the carbon burn step.

In an aspect, a method of regenerating a spent catalyst (e.g., comprising a transition metal and a catalyst support) comprising a chlorination step, followed by a carbon burn step, and then by a fluorination step, may further comprise a chlorine purging step prior to the carbon burn step. This purging step may comprise contacting the chlorinated spent catalyst with a chlorine purging stream comprising (or consisting essentially of, or consisting of) an inert gas. The inert gas may be helium, neon, argon, or nitrogen, or combinations of two or more of these materials; alternatively, helium; alternatively, neon; alternatively, argon; or alternatively, nitrogen. While not wishing to be bound by theory, it is believed that it may be beneficial to have a chlorine purging step prior to the carbon burn step, in order to reduce the corrosivity of the high-temperature carbon burn step on the reactor metallurgy.

Additionally, in some aspects, the chlorine purging stream may be substantially free of oxygen-containing compounds (e.g., oxygen and water), as discussed above in relation to the chlorination step. Hence, the chlorine purging step may be conducted in the presence of less than 100 ppmw of oxygen-containing compounds, or less than 50 ppmw, or less than 25 ppmw, or less than 10 ppmw, or less than 5 ppmw, or less than 3 ppmw.

Additionally, in some aspects, the chlorine purging stream may be substantially free of halogen-containing compounds, as discussed above in relation to the carbon burn step. Hence, the chlorine purging step may be conducted in the presence of less than 100 ppmw of halogen-containing compounds, or less than 50 ppmw, or less than 25 ppmw, or less than 10 ppmw, or less than 5 ppmw, or less than 3 ppmw.

The chlorine purging step may be performed at a chlorine purging temperature which generally may encompass the same temperature range as the chlorination temperature used in the chlorination step, although not limited thereto. Accordingly, the chlorine purging temperature often may be in a range from about 0° C. to about 500° C.; alternatively, from about 0° C. to about 400° C.; alternatively, from about 20° C. to about 300° C.; alternatively, from about 25° C. to about 250° C.; alternatively, from about 20° C. to about 150° C.; alternatively, from about 35° C. to about 300° C.; alternatively, from about 35° C. to about 200° C.; alternatively, from about 50° C. to about 250° C.; alternatively, from about 75° C. to about 250° C.; alternatively, from about 100° C. to about 300° C.; alternatively, from about 100° C. to about 250° C.; or alternatively, from about 150° C. to about 275° C. In these and other aspects, these temperature ranges also are meant to encompass circumstances where the chlorine purging step is conducted at a series of different temperatures, instead of at a single fixed temperature, falling within the respective ranges.

The duration of the chlorine purging step is not limited to any particular period of time. Typically, the chlorine purging step may be conducted in a time period ranging from as little as 30-45 minutes to as long as 48-72 hours (or more), but more typically, the chlorine purging step may be conducted in a time period that may be in a range from about 1 hour to about 48 hours, such as, for example, from about 1 hour to about 36 hours, from about 2 hours to about 36 hours, from about 2 hours to about 24 hours, or from about 2 hours to about 18 hours.

Alternatively, the chlorine purging step may be conducted for a time period sufficient to reduce the chlorine content of the outgoing purging effluent stream, after contacting the chlorinated spent catalyst, to less than 100 ppmw of chlorine-containing compounds (i.e., substantially chlorine-free). In some aspects consistent with the disclosure herein, the chlorine content of the outgoing chlorine purging effluent stream, after contacting the chlorinated spent catalyst, may be less than 50 ppmw, less than 25 ppmw, less than 10 ppmw, less than 5 ppmw, or less than 3 ppmw. While not wishing to be bound by theory, it is believed that it may be beneficial to have chlorine closely associated with the catalyst during the carbon burn step, but substantially no chlorine present in the free volume of the atmosphere surrounding the chlorinated spent catalyst (e.g., in the vessel containing the spent catalyst).

In an aspect, a method of regenerating a spent catalyst (e.g., comprising a transition metal and a catalyst support) comprising a chlorination step, followed by a carbon burn step, and then by a fluorination step, may further comprise a hydrocarbon treatment step prior to the carbon burn step. This hydrocarbon treatment step may comprise contacting the chlorinated spent catalyst with a hydrocarbon treatment stream comprising a hydrocarbon feed. The hydrocarbon treatment stream may be the same as a feed stream to an aromatization process. Hence, in some aspects, the hydrocarbon treatment stream may comprise $C_6$-$C_8$ alkanes and/or cycloalkanes.

The hydrocarbon treatment step may be performed at a hydrocarbon treatment temperature which generally may encompass the same temperature range as the temperature range used in the aromatization process. In some aspects, the hydrocarbon treatment temperature may be in a range from about 300° C. to about 600° C.; alternatively, from about 350° C. to about 600° C.; alternatively, from about 400° C. to about 600° C.; alternatively, from about 350° C. to about 550° C.; or alternatively, from about 450° C. to about 550° C. In these and other aspects, these temperature ranges also are meant to encompass circumstances where the hydrocarbon treatment step is conducted at a series of different temperatures, instead of at a single fixed temperature, falling within the respective ranges.

The duration of the hydrocarbon treatment step is not limited to any particular period of time. Typically, the hydrocarbon treatment step may be conducted in a time period ranging from as little as 30-45 minutes to as long as 48-72 hours (or more), but more typically, the hydrocarbon treatment step may be conducted in a time period that may be in a range from about 1 hour to about 48 hours, such as, for example, from about 1 hour to about 36 hours, from about 1 hour to about 24 hours, from about 2 hours to about 24 hours, or from about 2 hours to about 18 hours.

In various aspects contemplated herein, the methods of regenerating a spent catalyst may further include an optional oxygen purging step after the carbon burn step, but prior to the fluorination step. This oxygen purging step may comprise contacting the de-coked catalyst with an oxygen purging stream comprising (or consisting essentially of, or consisting of) an inert gas. The inert gas may be helium, neon, argon, or nitrogen, or combinations of two or more of these materials; alternatively, helium; alternatively, neon; alternatively, argon; or alternatively, nitrogen.

Additionally, in some aspects, the oxygen purging stream may be substantially free of oxygen-containing compounds (e.g., oxygen or water), as discussed above in relation to the chlorine purging step. Hence, the oxygen purging step may be conducted in the presence of less than 100 ppmw of oxygen-containing compounds, or less than 50 ppmw, or less than 25 ppmw, or less than 10 ppmw, or less than 5 ppmw, or less than 3 ppmw.

Additionally, in some aspects, the oxygen purging stream may be substantially free of halogen-containing compounds, as discussed above in relation to the chlorine purging step. Hence, the oxygen purging step may be conducted in the presence of less than 100 ppmw of halogen-containing compounds, or less than 50 ppmw, or less than 25 ppmw, or less than 10 ppmw, or less than 5 ppmw, or less than 3 ppmw.

The oxygen purging step may be performed at an oxygen purging temperature which generally may encompass the same temperature range as the chlorine purging temperature. Accordingly, the oxygen purging temperature may be in a range from about 0° C. to about 500° C.; alternatively, from about 0° C. to about 400° C.; alternatively, from about 15° C. to about 300° C.; alternatively, from about 25° C. to about 250° C.; alternatively, from about 20° C. to about 150° C.; alternatively, from about 35° C. to about 300° C.; alternatively, from about 35° C. to about 200° C.; alternatively, from about 50° C. to about 250° C.; alternatively, from about 75° C. to about 250° C.; alternatively, from about 100° C. to about 300° C.; alternatively, from about 100° C. to about 250° C.; or alternatively, from about 150° C. to about 275° C. In these and other aspects, these temperature ranges also are meant to encompass circumstances where the oxygen purging step is conducted at a series of different temperatures, instead of at a single fixed temperature, falling within the respective ranges.

The duration of the oxygen purging step is not limited to any particular period of time. Typically, the oxygen purging step may be conducted in a time period ranging from as little as 30-45 minutes to as long as 48-72 hours (or more), but more typically, the oxygen purging step may be conducted in a time period that may be in a range from about 1 hour to about 48 hours, such as, for example, from about 1 hour to about 36 hours, from about 2 hours to about 36 hours, from about 2 hours to about 24 hours, or from about 2 hours to about 18 hours.

Alternatively, the oxygen purging step may be conducted for a time period sufficient to reduce the oxygen content of the outgoing purging effluent stream, after contacting the de-coked catalyst, to less than 100 ppmw of oxygen-containing compounds (i.e., substantially oxygen-free). In some aspects consistent with the disclosure herein, the oxygen content of the outgoing oxygen purging effluent stream, after contacting the de-coked catalyst, may be less than 50 ppmw, less than 25 ppmw, less than 10 ppmw, less than 5 ppmw, or less than 3 ppmw. While not wishing to be bound by theory, it is believed that it may be beneficial to remove any oxygen-containing compounds, such as water, prior to the fluorination step.

In various aspects contemplated herein, the methods of regenerating a spent catalyst may further include an optional fluorine purging step after the fluorination step, but prior to a reducing step (discussed further herein below). This fluorine purging step may comprise contacting the de-coked and fluorinated catalyst with a fluorine purging stream comprising (or consisting essentially of, or consisting of) an inert gas. The inert gas may be helium, neon, argon, or nitrogen, or combinations of two or more of these materials; alternatively, helium; alternatively, neon; alternatively, argon; or alternatively, nitrogen. While not wishing to be bound by theory, it is believed that it may be beneficial to have a fluorine purging step after the fluorination step to reduce the corrosivity of excess or residual fluorine on the reactor metallurgy.

Additionally, in some aspects, the fluorine purging stream may be substantially free of oxygen-containing compounds (e.g., oxygen or water), as discussed above in relation to the chlorine purging step. Hence, the fluorine purging step may be conducted in the presence of less than 100 ppmw of oxygen-containing compounds, or less than 50 ppmw, or less than 25 ppmw, or less than 10 ppmw, or less than 5 ppmw, or less than 3 ppmw.

Additionally, in some aspects, the fluorine purging stream may be substantially free of halogen-containing compounds, as discussed above in relation to the chlorine purging step. Hence, the fluorine purging step may be conducted in the presence of less than 100 ppmw of halogen-containing compounds, or less than 50 ppmw, or less than 25 ppmw, or less than 10 ppmw, or less than 5 ppmw, or less than 3 ppmw.

The fluorine purging step may be performed at a fluorine purging temperature which generally may encompass the same temperature range as the chlorine purging temperature, although not limited thereto. Accordingly, the fluorine purging temperature often may be in a range from about 0° C. to about 500° C.; alternatively, from about 0° C. to about 400° C.; alternatively, from about 15° C. to about 300° C.; alternatively, from about 25° C. to about 250° C.; alternatively, from about 20° C. to about 150° C.; alternatively, from about 35° C. to about 300° C.; alternatively, from about 35° C. to about 200° C.; alternatively, from about 50° C. to about 250° C.; alternatively, from about 75° C. to about 250° C.; alternatively, from about 100° C. to about 300° C.; alternatively, from about 100° C. to about 250° C.; or alternatively, from about 150° C. to about 275° C. In these and other aspects, these temperature ranges also are meant to encompass circumstances where the fluorine purging step is conducted at a series of different temperatures, instead of at a single fixed temperature, falling within the respective ranges.

The duration of the fluorine purging step is not limited to any particular period of time. Typically, the fluorine purging step may be conducted in a time period ranging from as little as 30-45 minutes to as long as 48-72 hours (or more), but more typically, the fluorine purging step may be conducted in a time period that may be in a range from about 1 hour to about 48 hours, such as, for example, from about 1 hour to about 36 hours, from about 2 hours to about 36 hours, from about 2 hours to about 24 hours, or from about 2 hours to about 18 hours.

Alternatively, the fluorine purging step may be conducted for a time period sufficient to reduce the fluorine content of the outgoing purging effluent stream, after contacting the de-coked and fluorinated catalyst, to less than 100 ppmw of fluorine-containing compounds (i.e., substantially fluorine-free). In some aspects consistent with the disclosure herein, the fluorine content of the outgoing oxygen purging effluent stream, after contacting the de-coked and fluorinated catalyst, may be less than 50 ppmw, less than 25 ppmw, less than 10 ppmw, less than 5 ppmw, or less than 3 ppmw. While not wishing to be bound by theory, it is believed that it may be beneficial to have fluorine closely associated with the catalyst during the reducing step, but substantially no fluorine present in the free volume of the atmosphere surrounding the de-coked and fluorinated catalyst (e.g., in the vessel containing the catalyst).

The methods of regenerating a spent catalyst disclosed herein may further comprise a reducing step after the fluorination step, thereby forming a reactivated catalyst. This reducing step may comprise contacting the regenerated catalyst (e.g., a de-coked and fluorinated catalyst) with a reducing gas stream comprising molecular hydrogen. In addition to molecular hydrogen, the reducing gas stream may comprise an inert gas, i.e., the reducing gas stream may comprise (or consist essentially of, or consist of) molecular hydrogen and an inert gas. Typical inert gasses useful in the reducing step may encompass helium, neon, argon, nitrogen, and the like, and this includes combinations of two or more of these materials. In certain aspects, the reducing gas stream may comprise (or consist essentially of, or consist of) molecular hydrogen and nitrogen.

In some aspects, molecular hydrogen may be the major component of the reducing gas stream, while in other aspects, molecular hydrogen may be a minor component. For example, the reducing gas stream may comprise at least about 25 mole % molecular hydrogen, at least about 35 mole % molecular hydrogen, at least about 50 mole % molecular hydrogen, at least about 65 mole % molecular hydrogen, at least about 75 mole % molecular hydrogen, or 100 mole % molecular hydrogen. Accordingly, suitable ranges for the mole % of molecular hydrogen in the reducing gas stream may include, but are not limited to, the following ranges: from about 25 to 100 mole %, from about 50 to 100 mole %, from about 25 to 100 mole %, from about 35 to 100 mole %, from about 55 to 100 mole %, from about 25 to about 75 mole %, from about 35 to about 65 mole %, or from about 70 to 100 mole %, and the like.

The reducing step may be conducted at a variety of temperatures and time periods. For instance, the reducing step may be conducted at a peak reducing temperature in a range from about 300° C. to about 600° C.; alternatively, from about 300° C. to about 550° C.; alternatively, from about 400° C. to about 600° C.; alternatively, from about 350° C. to about 575° C.; alternatively, from about 400° C. to about 550° C.; or alternatively, from about 450° C. to about 550° C. In these and other aspects, these temperature ranges also are meant to encompass circumstances where the reducing step is conducted at a series of different temperatures (e.g., an initial reducing temperature, a peak reducing temperature), instead of at a single fixed temperature, falling within the respective ranges. For instance, the reducing step may start at an initial reducing temperature which is the same as the fluorine purging temperature or the fluorination temperature (e.g., in a range from about 0° C. to about 300° C., in range from about 20° C. to about 250° C., or in a range from 15° C. to about 50° C.). Subsequently, the temperature of the reducing step may be increased to a peak reducing temperature, for example, in a range from about 400° C. to about 600° C.

The duration of the reducing step is not limited to any particular period of time. Hence, the reducing step may be conducted, for example, in a time period ranging from as little as 1 hour to as long as 48-72 hours, or more. For example, the reducing step may be conducted in a time period that may be in a range from about 2 hours to about 48 hours, from about 3 hours to about 36 hours, from about 5 hours to about 36 hours, from about 2 hours to about 30 hours, or from about 10 hours to about 30 hours.

In one aspect, the reducing step may be performed ex-situ. In this aspect, the regenerated catalyst is converted to a reduced (or activated) catalyst according to the procedures described above. This reduction may occur at the catalyst regeneration site or another site. The reduced (or activated) catalyst may then be packaged under air or under an inert gas and is then stored prior to being loaded into the aromatization reactor and used in an aromatization reactor system. Prior to use, a reduction step may be performed to reduce any catalyst that became oxidized after the first reduction, for example during storage, transport and loading. This second reduction may require the same or less time than the in situ reduction described below.

In another aspect, the reducing step may be performed in situ. In this aspect, the regenerated catalyst is packaged after the regeneration process. The catalyst may be stored for an extended period of time prior to loading into an aromatization reactor. After loading into the aromatization reactor, the regenerated catalyst is then converted to a reduced (or activated) catalyst according to the procedures described above.

Other methods for regenerating spent catalysts comprising a transition metal and a catalyst support also are disclosed and described herein. In a particular aspect, a method of regenerating a spent catalyst may comprise (or consist essentially of, or consist of) (i) contacting the spent catalyst with a chlorine-containing stream comprising a chlorine-containing compound to produce a chlorinated spent catalyst; (ii) contacting the chlorinated spent catalyst with a chlorine purging stream comprising an inert gas; (iii) contacting the chlorinated spent catalyst with a decoking gas stream comprising oxygen to produce a de-coked catalyst; (iv) contacting the de-coked catalyst with a fluorine-containing stream comprising a fluorine-containing compound to produce a de-coked and fluorinated catalyst; and (v) contacting the de-coked and fluorinated catalyst with a fluorine purging stream comprising an inert gas. Moreover, other process steps may be conducted before, during, and/or after any of the steps listed in this method. Additionally, regenerated catalysts or subsequent reactivated catalysts produced in accordance with this method are within the scope of this disclosure and are encompassed herein.

Consistent with particular aspects of this invention, the methods disclosed herein may be conducted in a reactor vessel or system comprising a metal or stainless steel, and with substantially no damage to the metallurgy of the reactor vessel or system. In these and other aspects, the method may be conducted in the presence of stainless steel and with substantially no damage to the stainless steel, for example, removing iron from the stainless steel to result in a regenerated catalyst or reactivated catalyst having less than about 400 ppmw, less than about 300 ppmw, less than about 250 ppmw, or less than about 200 ppmw iron. Illustrative and non-limiting ranges include from about 5 ppmw to about 400 ppmw, from about 50 ppmw to about 300 ppmw, or from about 50 ppmw to about 250 ppmw iron, based on the weight of the regenerated catalyst or reactivated catalyst.

The regenerated catalysts or reactivated catalysts also may have low levels of carbon, including but not limited to the following representative ranges: from about 0.01 wt. % to about 1 wt. %, from about 0.1 wt. % to about 1 wt. %, from about 0.01 to about 0.5 wt. %, from about 0.1 wt. % to about 0.5 wt. %, from about 0.02 wt. % to about 1 wt. %, or from about 0.02 wt. % to about 0.5 wt. % carbon. Generally, the methods disclosed herein typically result in regenerated catalysts or reactivated catalysts containing from about 0.01 wt. % to about 5 wt. %, from about 0.05 wt. % to about 3 wt. %, from about 0.2 wt. % to about 4 wt. %, or from about 0.3 wt. % to about 1.3 wt. % chlorine. Likewise, the methods disclosed herein typically result in regenerated catalysts or reactivated catalysts containing from about 0.01 wt. % to about 5 wt. %, from about 0.05 wt. % to about 3 wt. %, from about 0.2 wt. % to about 4 wt. %, or from about 0.3 wt. % to about 1.3 wt. % fluorine. Optionally, the regenerated catalyst or reactivated catalyst may contain less than about 0.1 wt. % of barium, less than about 0.01 wt. % barium, or no barium (no measurable amount).

The methods provided herein are very effective at restoring catalytic activity to a spent catalyst. For instance, and beneficially, the reactivated catalyst or regenerated catalyst may be characterized by a TEOR (end of run temperature) within about 50° F., within about 40° F., within about 30° F., or within about 20° F., of the TEOR of a fresh reference catalyst (from the same production run (or batch) of catalyst, tested on the same equipment, and under the same test method and conditions). Additionally or alternatively, the reactivated catalyst or regenerated catalyst may be characterized by a TSOR (start of run temperature) within about 50° F., within about 40° F., within about 30° F., or within about 20° F., of the TSOR of a fresh reference catalyst (from the same production run (or batch) of catalyst, tested on the same equipment, and under the same test method and conditions).

Moreover, the reactivated catalyst or regenerated catalyst may be characterized by relatively low fouling rates, as described herein. The reactivated catalyst or regenerated catalyst may have a fouling rate (FR, slope of temperature versus time) ranging from about 0.01° F./hr to about 0.25° F./hr, from about 0.02° F./hr to about 0.2° F./hr, or from about 0.03° F./hr to about 0.15° F./hr. Beneficially, the reactivated catalyst or regenerated catalyst may be characterized by an aromatics selectivity or benzene+toluene selectivity in range from about 0.88 to about 0.95, or from about 0.89 to about 0.94. In some instances, and unexpectedly, the aromatics selectivity or benzene+toluene selectivity may be greater than or within about 2 percent of the selectivity of the fresh reference catalyst.

Reforming Processes with Aromatization Catalysts

Also encompassed herein are various processes for reforming hydrocarbons. One such reforming process may comprise (or consist essentially of, or consist of):

(A) contacting a hydrocarbon feed with an aromatization catalyst comprising a transition metal and a catalyst support under reforming conditions in a metal reactor system to produce an aromatic product;

(B) performing step (A) for a time period sufficient to form a spent catalyst;

(C) contacting the spent catalyst with a chlorine-containing stream comprising a chlorine-containing compound to produce a chlorinated spent catalyst;

(D) contacting the chlorinated spent catalyst with a decoking gas stream comprising oxygen to produce a de-coked catalyst; and (E) contacting the de-coked catalyst with a fluorine-containing steam comprising a fluorine-containing compound.

Generally, the features of any of the reforming processes disclosed herein (e.g., the metal reactor system, the hydrocarbon feed, the aromatization catalyst, the transition metal, the catalyst support, the reforming conditions, the fluorine-containing stream, the conditions under which the fluorination step is conducted, the chlorine-containing stream, the conditions under which the chlorination step is conducted, the decoking gas stream, the conditions under which the decoking step is conducted, among others) are independently described herein, and these features may be combined in any combination to further describe the disclosed reforming processes. Moreover, other process steps may be conducted before, during, and/or after any of the steps listed in the disclosed reforming processes, unless stated otherwise.

The chlorination, carbon burn, and fluorination steps (steps (C)-(E)) are discussed herein above. Any aspects and features of the chlorination step and/or the carbon burn step and/or the fluorination step (as well as other steps that may be conducted before, during and/or after the chlorination step and/or the carbon burn step and/or the fluorination step) described herein may be utilized in the processes for reforming hydrocarbons and, accordingly, are encompassed herein.

In these reforming processes, step (A) may comprise contacting a hydrocarbon feed with an aromatization catalyst under reforming conditions in a metal reactor system to produce an aromatic product. The metal reactor systems for reforming and the respective reforming conditions are well known to those of skill in the art and are described, for example, in U.S. Pat. Nos. 4,456,527, 5,389,235, 5,401,386, 5,401,365, 6,207,042, 6,548,030, 7,544,335, 7,582,272, 7,932,425, 8,119,203, and 9,085,736, which are incorporated herein by reference in their entirety.

Likewise, typical hydrocarbon feeds are disclosed in these references. Often, the hydrocarbon feed may be a naphtha stream or light naphtha stream. In certain aspects, the hydrocarbon feed may comprise $C_6$-$C_8$ alkanes and/or cycloalkanes (e.g., hexane, heptane, and cyclohexane).

Step (B) in the reforming processes indicates that step (A) may be performed for a time period sufficient for the aromatization catalyst to become "spent." As discussed herein above, a "spent" catalyst is typically a catalyst that has unacceptable performance in one or more of catalyst activity, hydrocarbon feed conversion, yield to a desired product(s), selectivity to a desired product(s), or an operating parameter, such as output/production rate or reforming temperature, although not limited thereto. Once the aromatization catalyst is "spent," the regeneration steps (C), (D), and (E), amongst others, may be performed.

In an aspect, the reforming process may be an in situ process, for example, steps (A)-(E) may be performed in the same metal reactor system. However, in an alternative aspect, the catalyst regeneration steps (C)-(E) may be conducted external to the reactor system, such as in another metal vessel and/or location. For instance, the chlorination, carbon burn, and fluorination steps may be conducted in a metal reactor that is not in the reforming reactor system. In another aspect, the reforming process may further comprise a step of reactivating the catalyst after step (E). Any catalyst reactivated or any catalyst regenerated by these processes is considered within the scope of this disclosure and encompassed herein.

Transition Metal Based Catalysts

Consistent with aspects disclosed herein, and the various methods described herein above and below, the aromatization catalyst (fresh, spent, regenerated, or reactivated) may comprise a transition metal and a catalyst support. The catalyst support typically may comprise an inorganic oxide, examples of which may include, but are not limited to, bound medium and/or large pore zeolites (aluminosilicates), amorphous inorganic oxides, as well as mixtures thereof. Large pore zeolites often may have average pore diameters in a range of from about 7 Å to about 12 Å, and non-limiting examples of large pore zeolites include L-zeolite, Y-zeolite, mordenite, omega zeolite, beta zeolite, and the like. Medium pore zeolites often may have average pore diameters in a range of from about 5 Å to about 7 Å. Amorphous inorganic oxides may include, but are not limited to, aluminum oxide, silicon oxide, titania, and combinations thereof.

The term "zeolite" generally refers to a particular group of hydrated, crystalline metal aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms may be equal to 2. The framework exhibits a negative electrovalence that typically may be balanced by the inclusion of cations within the crystal, such as metals, alkali metals, alkaline earth metals, and/or hydrogen.

In some aspects, the catalyst support may comprise an L-type zeolite. L-type zeolite supports are a sub-group of zeolitic supports, which may contain mole ratios of oxides in accordance with the formula: $M_{2/n}OAl_2O_3xSiO_2yH_2O$. In this formula, "M" designates an exchangeable cation (one or more) such as barium, calcium, cerium, lithium, magnesium, potassium, sodium, strontium, cesium, and/or zinc, as well as non-metallic cations like hydronium and ammonium ions, which may be replaced by other exchangeable cations without causing a substantial alteration of the basic crystal structure of the L-type zeolite. The "n" in the formula represents the valence of "M"; "x" is 2 or greater; and "y" is the number of water molecules contained in the channels or interconnected voids of the zeolite.

In one aspect, the catalyst support may comprise a bound potassium L-type zeolite, also referred to as a KL-zeolite, while in another aspect, the catalyst support may comprise a barium ion-exchanged L-zeolite. As used herein, the term "KL-zeolite" refers to L-type zeolites in which the principal cation M incorporated in the zeolite is potassium. A KL-zeolite may be cation-exchanged (e.g., with barium or cesium) or impregnated with a transition metal and one or more halides to produce a transition metal impregnated, halided zeolite or a KL supported transition metal-halide zeolite catalyst.

In the catalyst support, the zeolite may be bound with a binder, non-limiting examples of which may include silica, alumina, magnesia, boria, titania, zirconia, various clays, and the like, including mixed oxides thereof, as well as mixtures thereof. For example, the catalyst support may comprise a binder comprising alumina, silica, a mixed oxide thereof, or a mixture thereof. The zeolite may be bound with the binder using any method known in the art.

The aromatization catalyst may comprise a transition metal, and non-limiting examples of suitable transition metals may include iron, cobalt, nickel, ruthenium, rhodium, rhenium, palladium, osmium, iridium, platinum, gold, silver, copper, and the like, or a combination of two or more transition metals. In one aspect, the transition metal may comprise a Group 8-11 transition metal or a Group 8-10 transition metal (one or more), while in another aspect, the transition metal may comprise platinum (Pt).

In one aspect, the catalyst (fresh, spent, regenerated, or reactivated) may comprise from about 0.1 wt. % to about 10 wt. % transition metal. In another aspect, the catalyst may comprise from about 0.3 wt. % to about 5 wt. % transition metal. In yet another aspect, the catalyst may comprise from about 0.3 wt. % to about 3 wt. % transition metal, or from about 0.5 wt. % to about 2 wt. % transition metal. These weight percentages are based on the weight of the respective "dry" catalyst.

In circumstances where the transition metal comprises platinum, the catalyst may comprise from about 0.1 wt. % to about 10 wt. % platinum; alternatively, from about 0.3 wt. % to about 5 wt. % platinum; alternatively, from about 0.3 wt. % to about 3 wt. % platinum; or alternatively, from about 0.5 wt. % to about 2 wt. % platinum. In a particular aspect contemplated herein, the catalyst may comprise platinum on a KL-zeolite.

While not being limited thereto, the catalyst support may comprise from about 5 wt. % to about 35 wt. % binder. For example, the catalyst may comprise from about 5 wt. % to about 30 wt. %, or from about 10 wt. % to about 30 wt. % binder.

In an aspect, the aromatization catalyst (fresh, spent, regenerated, or reactivated) may further comprise a halogen, such as chlorine, fluorine, bromine, iodine, or a combination of two or more halogens. For example, the catalyst may comprise chlorine, or fluorine, or both chlorine and fluorine. Chlorine may be present in the catalyst in an amount of from about 0.01 wt. % to about 5 wt. %, from about 0.05 wt. % to about 3 wt. %, or from about 0.3 wt. % to about 1.3 wt. %. Likewise, the catalyst may comprise from about 0.01 wt. % to about 5 wt. % fluorine, from about 0.05 wt. % to about 3 wt. % fluorine, or from about 0.3 wt. % to about 1.3 wt. % fluorine. In certain aspects, the catalyst comprises chlorine and fluorine, and typically, the molar ratio of chlorine:fluorine may be in the range of from about 0.5:1 to about 4:1. Other suitable molar ratios of Cl:F may include the following non-limiting ranges: from about 1:1 to about 4:1, from about 0.5:1 to about 3:1, from about 1:1 to about 3:1, from about 0.5:1 to about 2:1, or from about 1:1 to about 2.5:1.

Examples of representative and non-limiting catalysts that are encompassed herein include those disclosed in U.S. Pat.

Nos. 5,196,631, 6,190,539, 6,406,614, 6,518,470, 6,812,180, 7,153,801, and 7,932,425, the disclosures of which are incorporated herein by reference in their entirety.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

Weight percentages of Pt, Cl, F, and Fe were determined using X-ray fluorescence (XRF), and are based on the total weight of the aromatization catalyst, unless stated otherwise. Carbon (wt. %) was determined by CHNS analyzer (Carlo Erba). Platinum dispersions were determined by CO Chemisorption.

Regenerated catalysts in some of the examples that follow were tested for their respective fouling rates (abbreviated FR, units of ° F./hr), which correlate to their activities by the formula, y=FR*t+TSOR, where y is temperature, FR is the fouling rate, t is time, and TSOR is the initial start of run temperature. The FR of a regenerated catalyst sample was determined by plotting the temperature required to maintain a total aromatics yield at 63 wt. % over time at standard test conditions, as described later herein. The FR's were then determined from the calculated slopes fit to the resulting data. The total time on stream was typically 40 hr, and the end of run temperature (abbreviated TEOR) also was determined.

In each of the examples, the following standard testing procedures were utilized. The catalysts were ground and sieved to about 25-45 mesh, and 1 g of the sieved catalyst was placed in a ¼-inch OD stainless steel reactor vessel in a temperature controlled furnace. After reducing the catalyst under flowing molecular hydrogen, a feed stream of aliphatic hydrocarbons and molecular hydrogen was introduced to the reactor vessel at a feed rate of 22 mL/min, a pressure of 100 psig, a $H_2$:hydrocarbon molar ratio of 1.3:1, and a liquid hourly space velocity (LHSV) of 12 $hr^{-1}$ to obtain catalyst performance data over time. The aliphatic hydrocarbon feed contained from 22 to 26 wt. % n-hexane, 4 to 8 wt. % n-heptane, 33 to 37 wt. % $C_6$ iso-paraffins, 17 to 21 wt. % $C_7$ iso-paraffins, 6 to 10 wt. % $C_8$ iso-paraffins, with the balance attributable to $C_6$ and $C_7$ olefins, naphthenes, and aromatics. The reactor effluent composition was analyzed by gas chromatography to determine the total aromatics and the benzene+toluene selectivity.

Examples 1-11

In Examples 1-11, experiments were conducted to demonstrate the effectiveness of various processes and steps in regenerating a spent catalyst, with the performance of a fresh aromatization catalyst used as a target baseline. The fresh aromatization catalyst was a Pt/KL-zeolite containing approximately 1 wt. % platinum, 0.85 wt. % Cl, and 0.70 wt. % F, with a BET surface area of approximately 177.5 $m^2/g$, a mercury intruded pore volume of 0.19 cc/g, and a micropore volume of 0.0615 cc/g. The source of the spent catalyst was the fresh catalyst, but after it had been deactivated after long-term use in an aromatization process. Prior to usage in these examples, the spent catalyst was subjected to a mild partial decoking treatment to remove unreacted hydrocarbons and light carbonaceous deposits from the catalyst.

Example 1 used the following regeneration procedure. Approximately 42 g of the spent catalyst was charged to a new metal fixed-bed reactor (stainless steel 347), unless noted otherwise, then contacted at 400° F. with a nitrogen gas stream (1500 mL/min) for 12 hr, then contacted at 400° F. with a chlorine-containing gas stream containing nitrogen (1463 mL/min) and chlorine gas (37 mL/min) for 3 hr, then contacted at 400° F. with a nitrogen gas stream (1463 mL/min) for 3 hr, then contacted at 750° F. with a decoking gas stream containing a mixture of air (75 mL/min) and nitrogen (1425 mL/min) for 44 hr, then contacted at 400° F. with a fluorine-containing gas stream containing nitrogen (1350 mL/min) and fluorine gas (147 mL/min) for 3 hr, and then contacted at 400° F. with a nitrogen gas stream (1353 mL/min) for 3 hr.

Figure 1B:
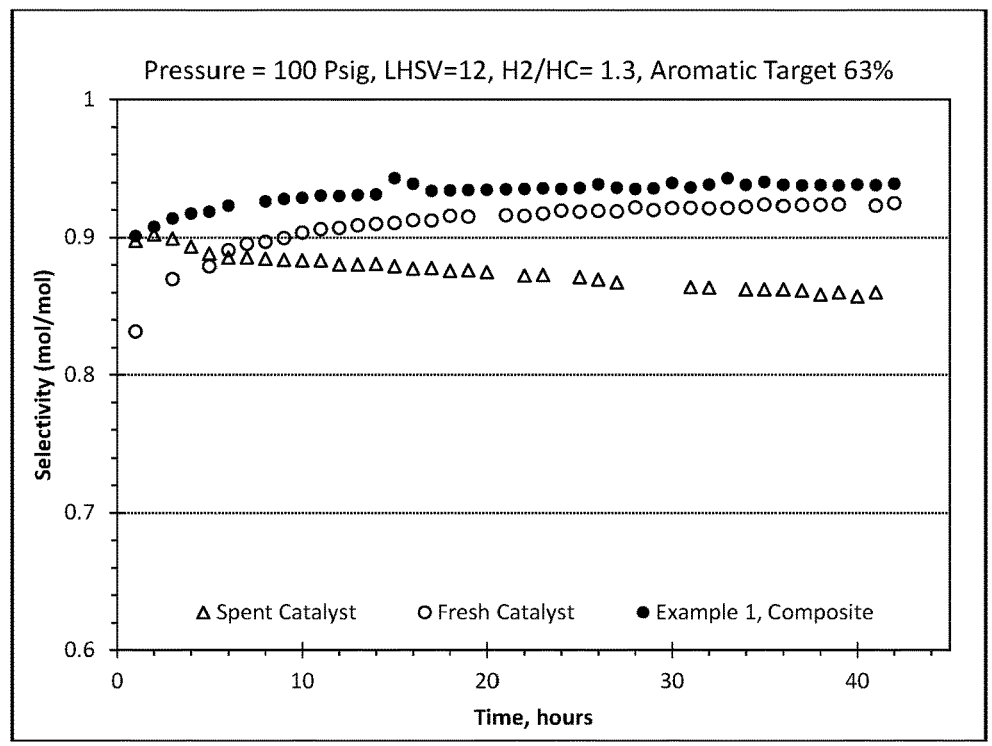
FIG. 1B presents a plot of the catalyst selectivity versus reaction time for the regenerated catalyst of Example 1, compared with the fresh catalyst and spent catalyst.

FIG. 1A and FIG. 1B are plots of the yield adjusted temperature versus reaction time and the selectivity versus reaction time, respectively, for the regenerated catalyst of Example 1 compared with the fresh catalyst and spent catalyst. Unexpectedly, the regeneration process used in Example 1 restored the catalyst activity almost to that of the fresh catalyst, and the benzene+toluene selectivity was equivalent to or better than that of the fresh catalyst.

Figure 2A:
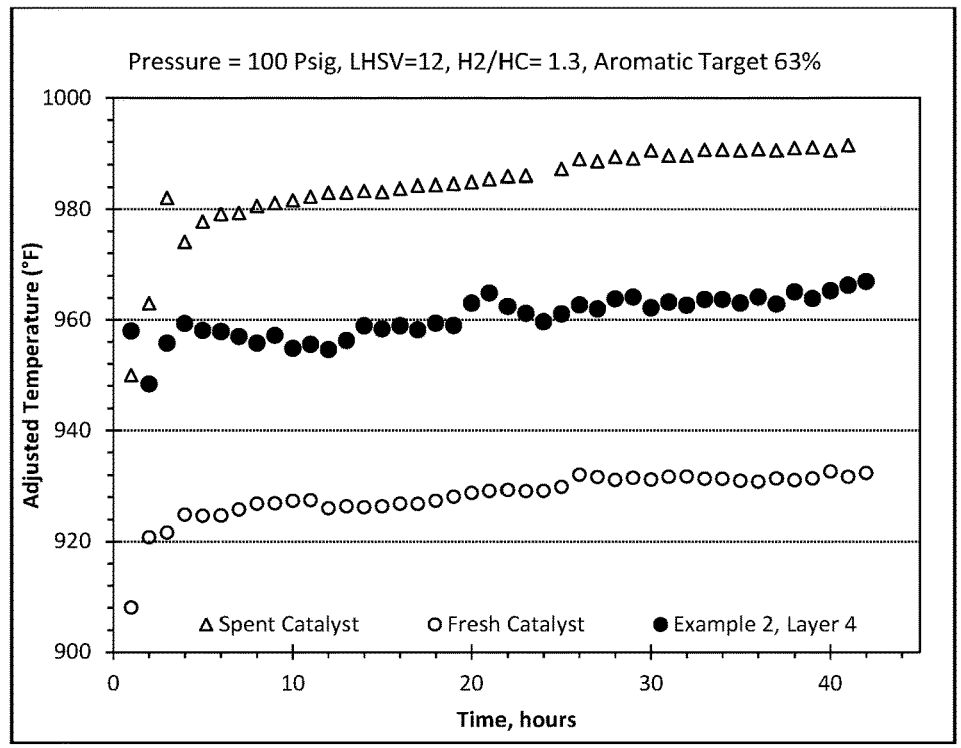
FIG. 2A presents a plot of the yield adjusted temperature versus reaction time for the regenerated catalyst of Example 2, compared with the fresh catalyst and spent catalyst.
Figure 2B:
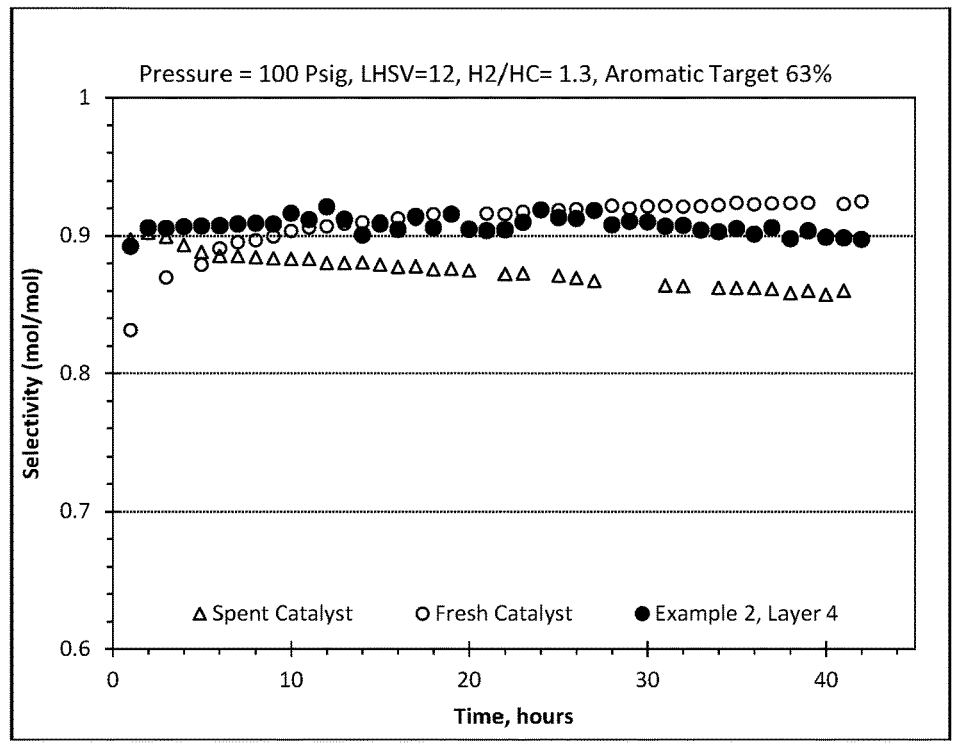
FIG. 2B presents a plot of the catalyst selectivity versus reaction time for the regenerated catalyst of Example 2, compared with the fresh catalyst and spent catalyst.

Example 2 was performed similarly to that of Example 1, except that no carbon burn or decoking step was used. FIG. 2A and FIG. 2B are plots of the yield adjusted temperature versus reaction time and the selectivity versus reaction time, respectively, for the regenerated catalyst of Example 2 compared with the fresh catalyst and spent catalyst. Table I summarizes certain properties of the regenerated catalysts and key performance criteria derived from the figures. In Table I, the amounts of Cl and F on the regenerated catalyst are in wt. %, the amount of carbon is in wt. %, and the amount of iron is in ppmw (ppm by weight). After each regeneration test, the catalyst bed was split into four layers: Layer 1 was the top layer, Layer 4 was the bottom layer, and the composite was a physical mix of Layers 1-4. For some of the experiments, every layer was tested, and for other experiments, only one layer was tested.

Referring back to Example 2, as compared to the spent catalyst, some activity and selectivity were recovered using the regeneration procedure of Example 2; however, the catalyst fouled at nearly the same rate as the spent catalyst and the regeneration procedure did not remove any appreciable amount of carbon from the spent catalyst.

Figure 3A:
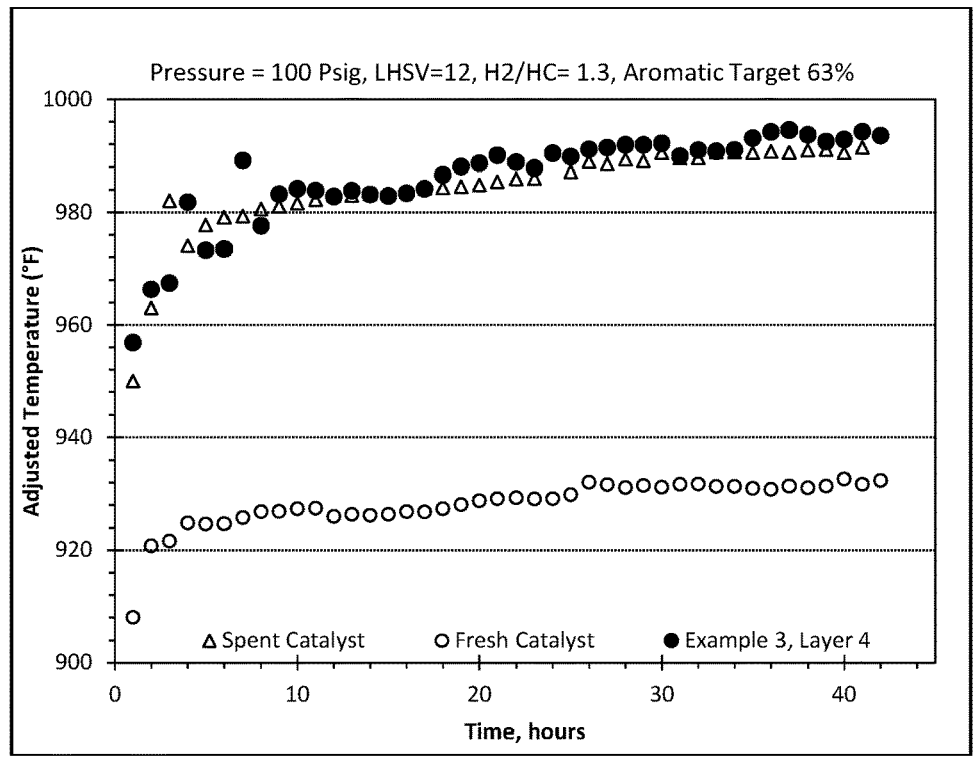
FIG. 3A presents a plot of the yield adjusted temperature versus reaction time for the regenerated catalyst of Example 3, compared with the fresh catalyst and spent catalyst.
Figure 3B:
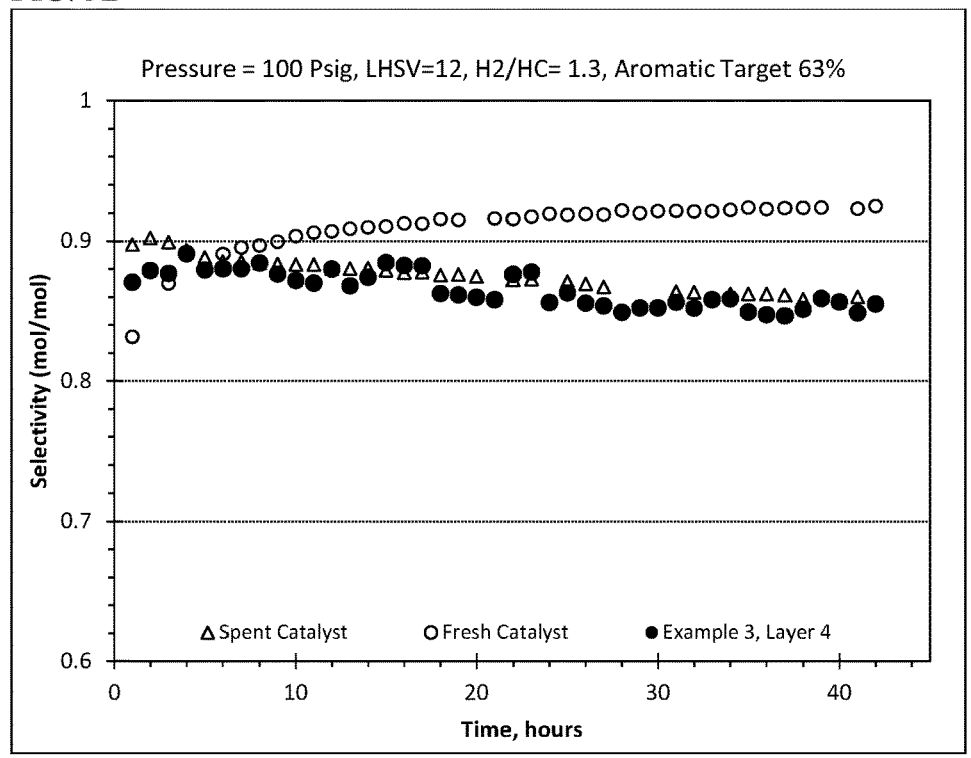
FIG. 3B presents a plot of the catalyst selectivity versus reaction time for the regenerated catalyst of Example 3, compared with the fresh catalyst and spent catalyst.

Example 3 was performed similarly to that of Example 1, except that no halogenation steps were used (drying step with nitrogen followed by carbon burn). FIG. 3A and FIG. 3B are plots of the yield adjusted temperature versus reaction time and the selectivity versus reaction time, respectively, for the regenerated catalyst of Example 3 compared with the fresh catalyst and spent catalyst. As compared to the spent catalyst, no activity and selectivity were recovered using the regeneration procedure of Example 3.

Figure 4A:
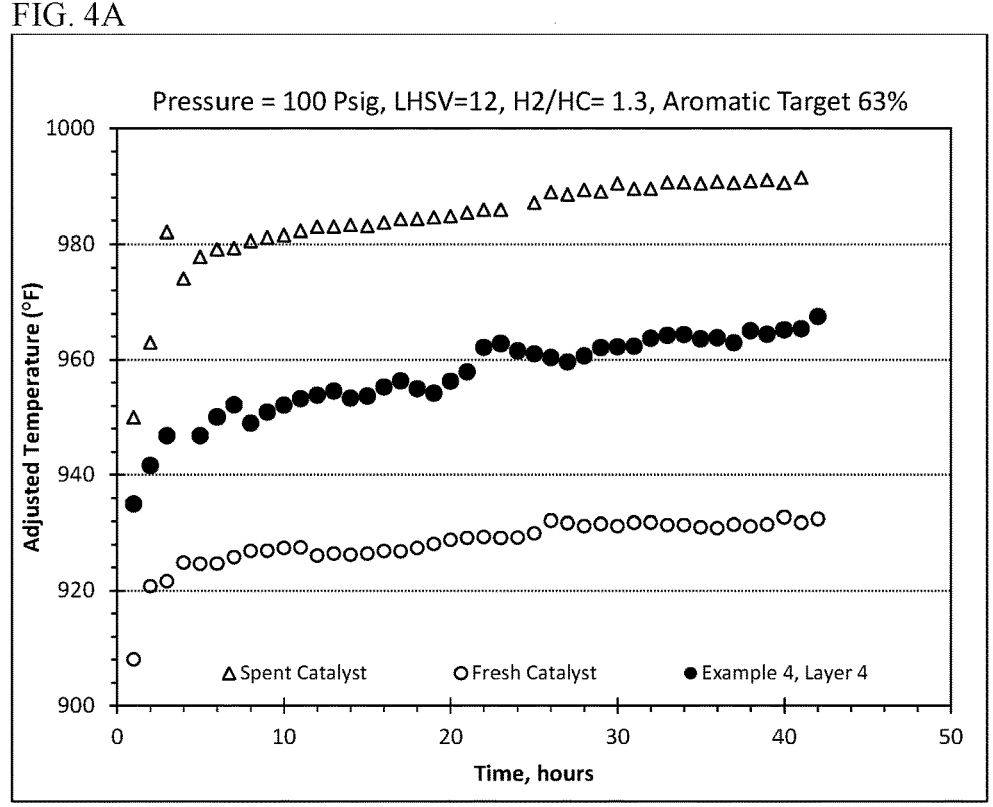
FIG. 4A presents a plot of the yield adjusted temperature versus reaction time for the regenerated catalyst of Example 4, compared with the fresh catalyst and spent catalyst.
Figure 4B:
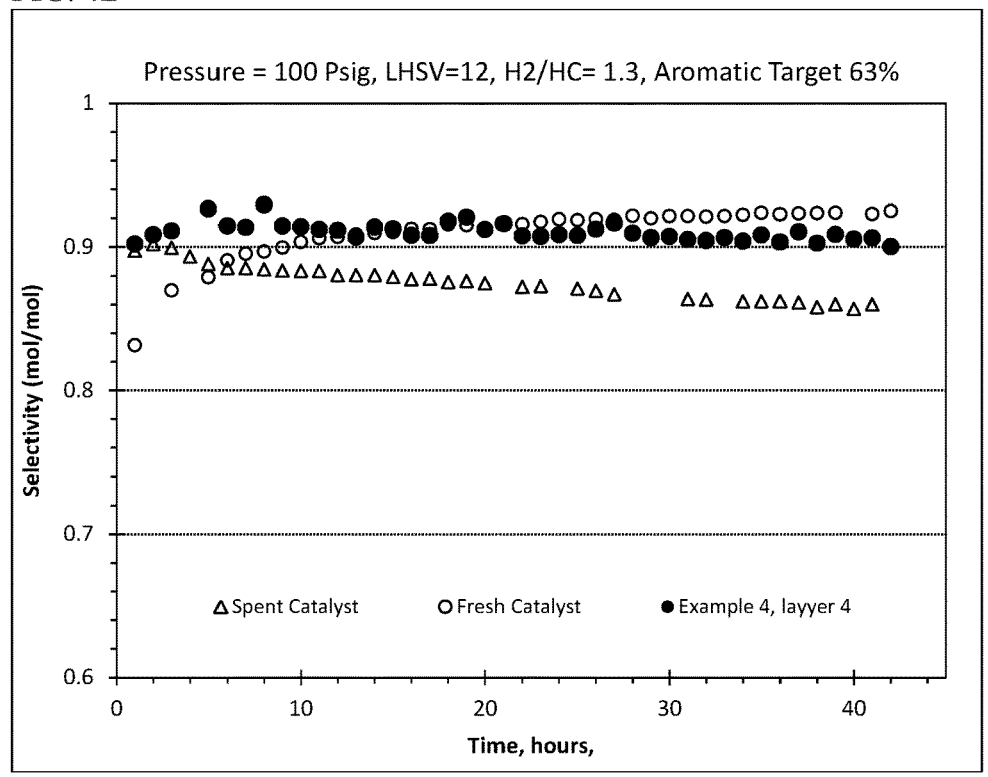
FIG. 4B presents a plot of the catalyst selectivity versus reaction time for the regenerated catalyst of Example 4, compared with the fresh catalyst and spent catalyst.

Example 4 was performed similarly to that of Example 1, except that no fluorination step was used. FIG. 4A and FIG. 4B are plots of the yield adjusted temperature versus reaction time and the selectivity versus reaction time, respectively, for the regenerated catalyst of Example 4 compared with the fresh catalyst and spent catalyst. As compared to the spent catalyst, some activity and selectivity were recovered using the regeneration procedure of Example 4; however, the catalyst fouled at a higher rate than that of the spent catalyst, indicating rapid deactivation of the regenerated catalyst of Example 4.

Figure 5A:
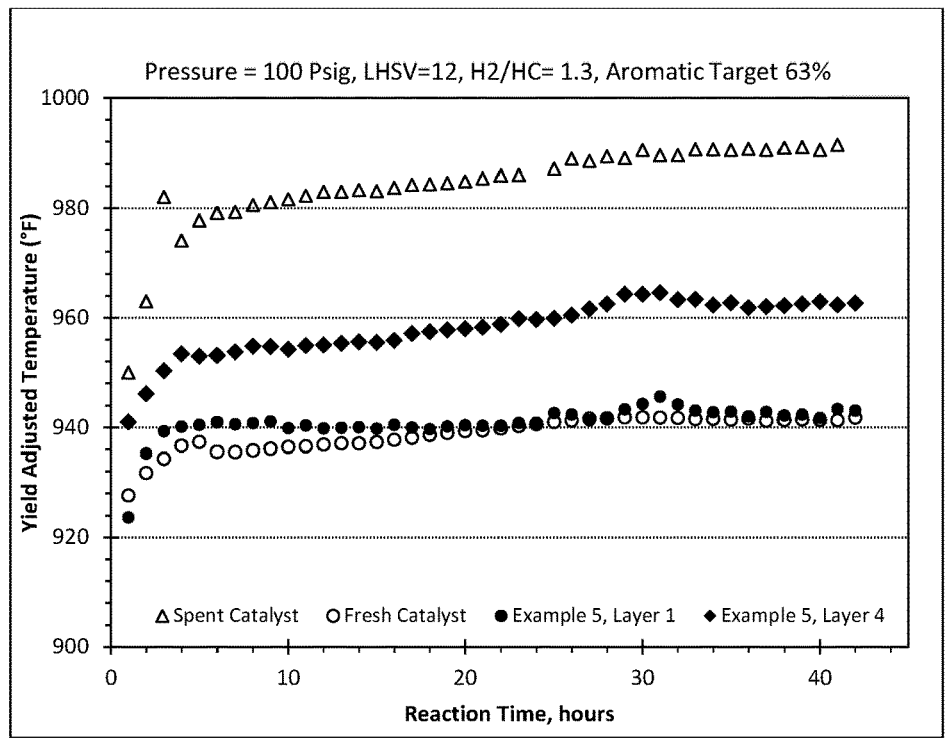
FIG. 5A presents a plot of the yield adjusted temperature versus reaction time for the regenerated catalyst of Example 5, compared with the fresh catalyst and spent catalyst.
Figure 5B:
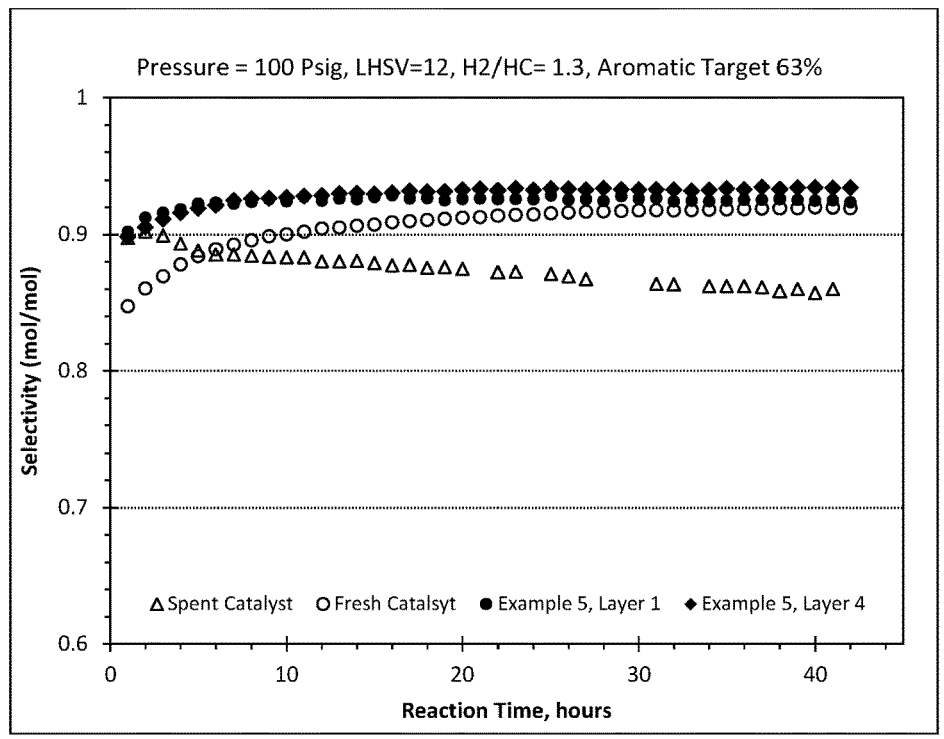
FIG. 5B presents a plot of the catalyst selectivity versus reaction time for the regenerated catalyst of Example 5, compared with the fresh catalyst and spent catalyst.

Example 5 was performed similarly to that of Example 1, except that chlorine and fluorine were co-impregnated, followed by a nitrogen purge, and then a carbon burn step was used. FIG. 5A and FIG. 5B are plots of the yield adjusted temperature versus reaction time and the selectivity versus reaction time, respectively, for the regenerated catalyst of Example 5 compared with the fresh catalyst and spent catalyst. As compared to the spent catalyst, the activity and selectivity were significantly improved using the regeneration procedure of Example 5 in the new reactor; however, the fouling rate was higher than that of Example 7, as shown in Table I.

Figure 6A:
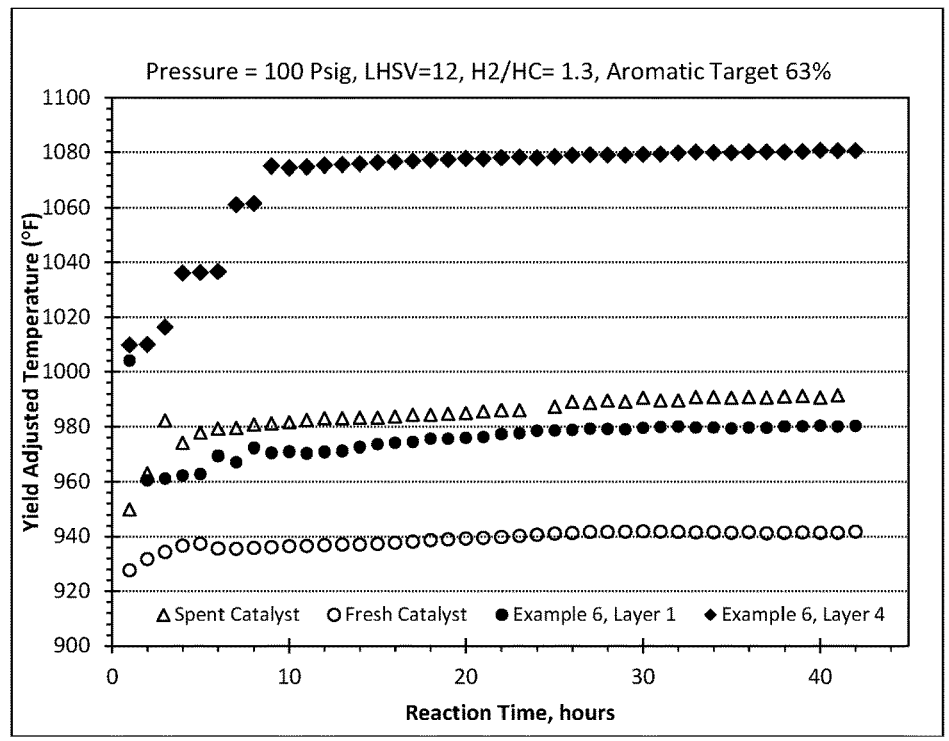
FIG. 6A presents a plot of the yield adjusted temperature versus reaction time for the regenerated catalyst of Example 6, compared with the fresh catalyst and spent catalyst.
Figure 6B:
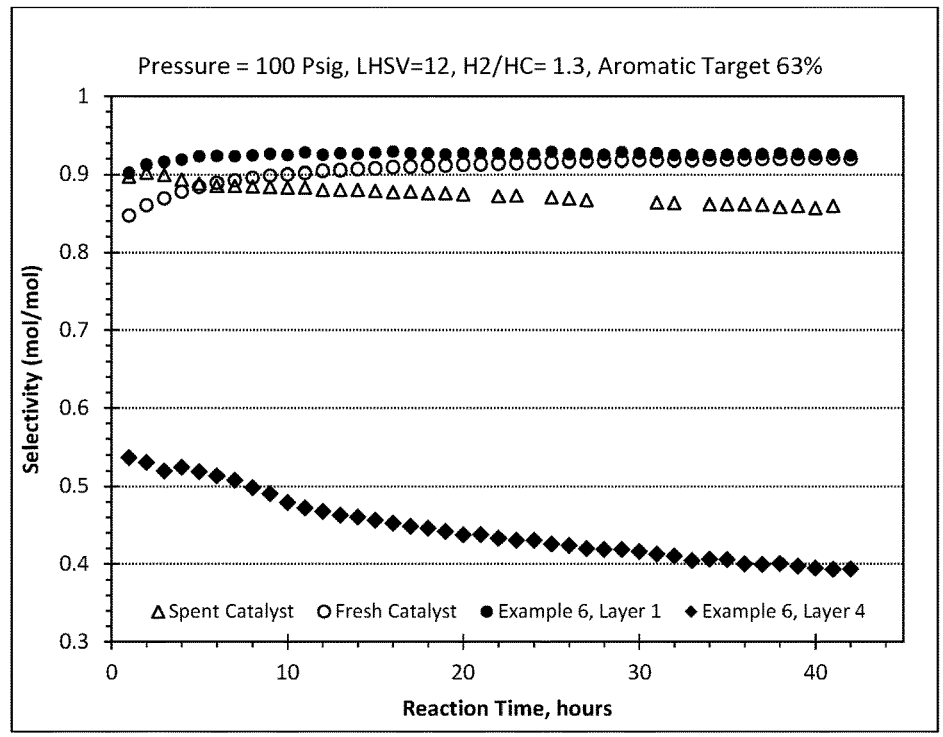
FIG. 6B presents a plot of the catalyst selectivity versus reaction time for the regenerated catalyst of Example 6, compared with the fresh catalyst and spent catalyst.

Example 6 used the same procedure as that of Example 5, but with the used reactor from Example 5. FIG. 6A and FIG. 6B are plots of the yield adjusted temperature versus reaction time and the selectivity versus reaction time, respectively, for the regenerated catalyst of Example 6 compared with the fresh catalyst and spent catalyst. When the reactor was used for a second time, the regenerated catalyst of Example 6 was unusable. For instance, the top of the bed was dead (Layer 1, 470 ppmw Fe), and the overall amount of iron contamination in the catalyst was unacceptably high, indicating unacceptable corrosion using this regeneration procedure. Moreover, no appreciable amount of carbon was removed from the spent catalyst.

Figure 7A:
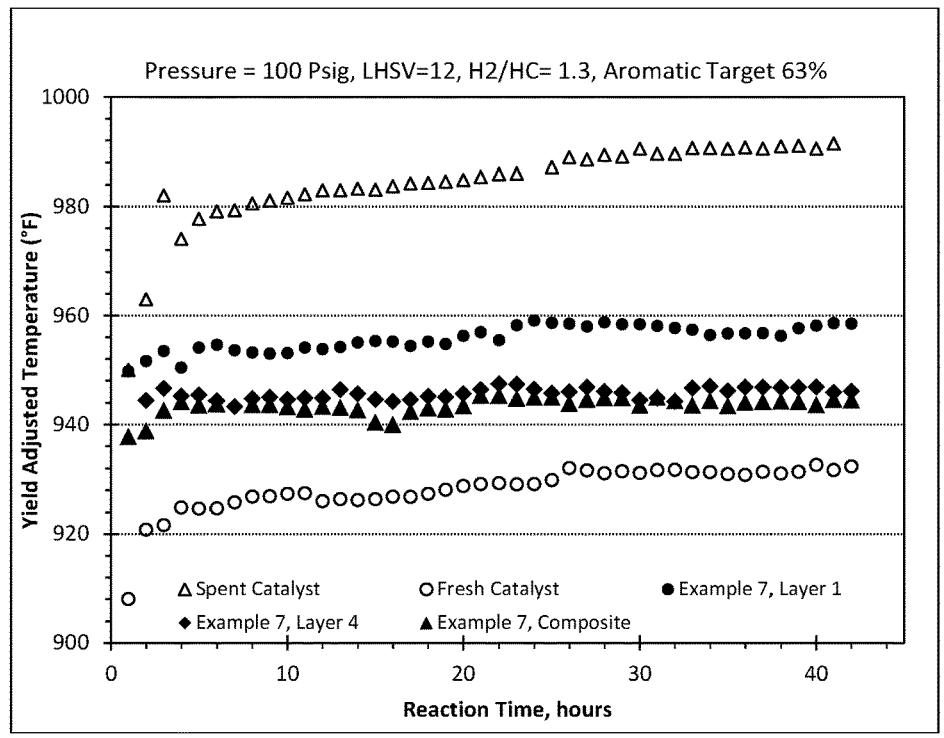
FIG. 7A presents a plot of the yield adjusted temperature versus reaction time for the regenerated catalyst of Example 7, compared with the fresh catalyst and spent catalyst.
Figure 7B:
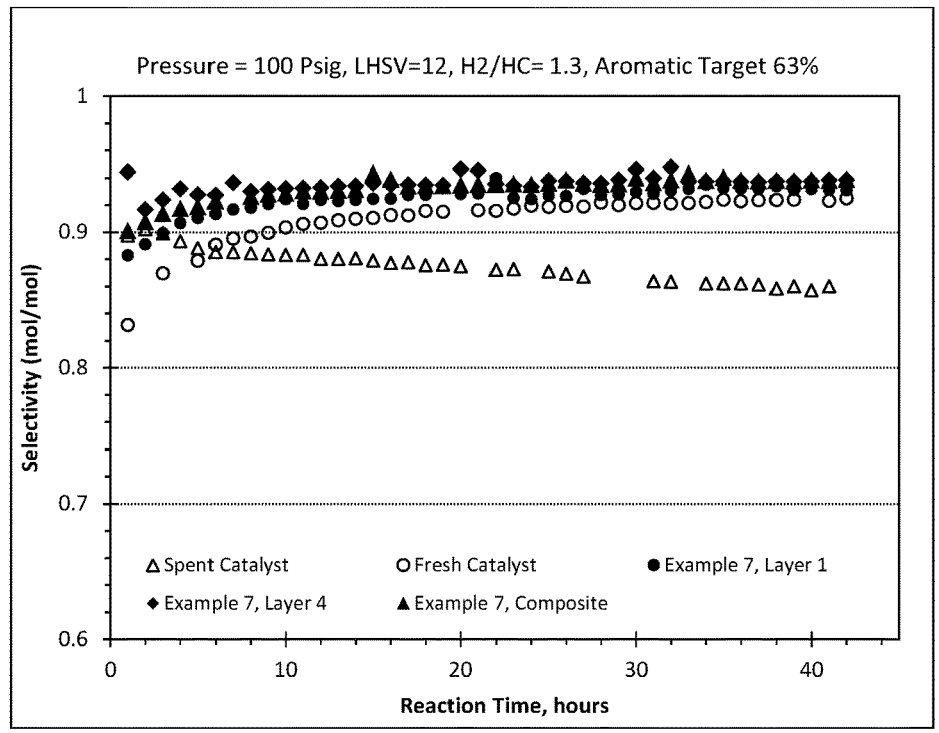
FIG. 7B presents a plot of the catalyst selectivity versus reaction time for the regenerated catalyst of Example 7, compared with the fresh catalyst and spent catalyst.

Example 7 was performed using the same procedure as that of Example 1. FIG. 7A and FIG. 7B are plots of the yield adjusted temperature versus reaction time and the selectivity versus reaction time, respectively, for the regenerated catalyst of Example 7 compared with the fresh catalyst and spent catalyst. Surprisingly, both the top and bottom layers were regenerated with low fouling rates (Table I), and benzene+ toluene selectivity's were comparable to or better than the fresh catalyst.

Figure 8A:
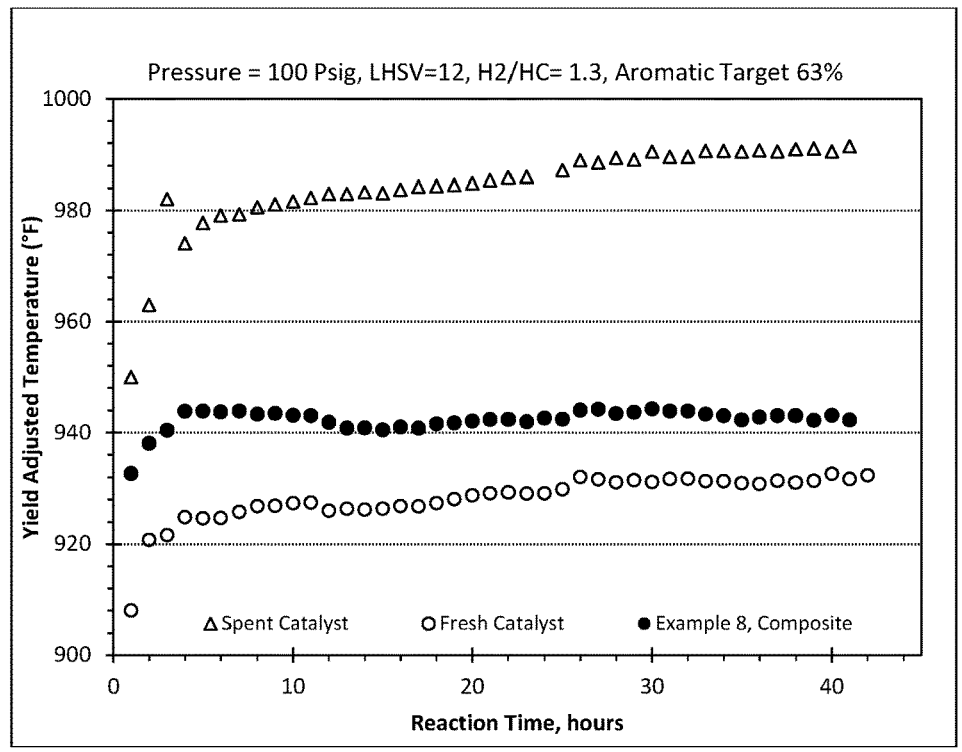
FIG. 8A presents a plot of the yield adjusted temperature versus reaction time for the regenerated catalyst of Example 8, compared with the fresh catalyst and spent catalyst.
Figure 8B:
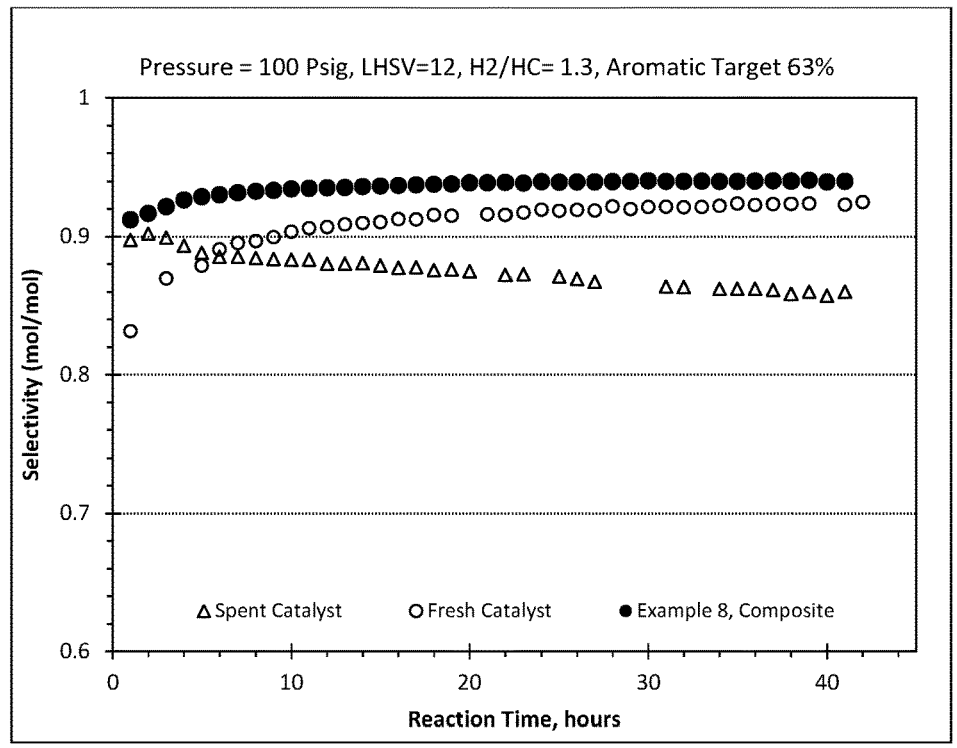
FIG. 8B presents a plot of the catalyst selectivity versus reaction time for the regenerated catalyst of Example 8, compared with the fresh catalyst and spent catalyst.

Example 8 used the same procedure as that of Example 7, but with the used reactor from Example 7. FIG. 8A and FIG. 8B are plots of the yield adjusted temperature versus reaction time and the selectivity versus reaction time, respectively, for the regenerated catalyst of Example 8 compared with the fresh catalyst and spent catalyst. When the reactor was used for a second time, the regenerated catalyst of Example 8 unexpectedly performed the same as that of Example 7, indicating that there was no significant corrosion of the metal reactor. The iron levels in the regenerated catalysts of Examples 7 and 8 were similar.

Figure 9A:
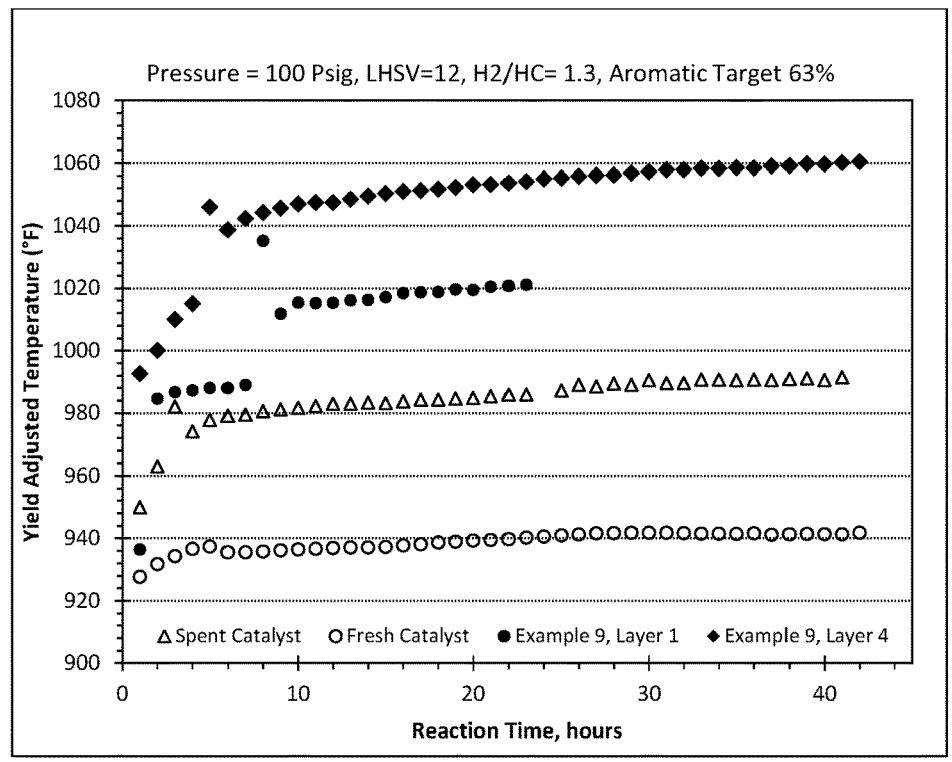
FIG. 9A presents a plot of the yield adjusted temperature versus reaction time for the regenerated catalyst of Example 9, compared with the fresh catalyst and spent catalyst.
Figure 9B:
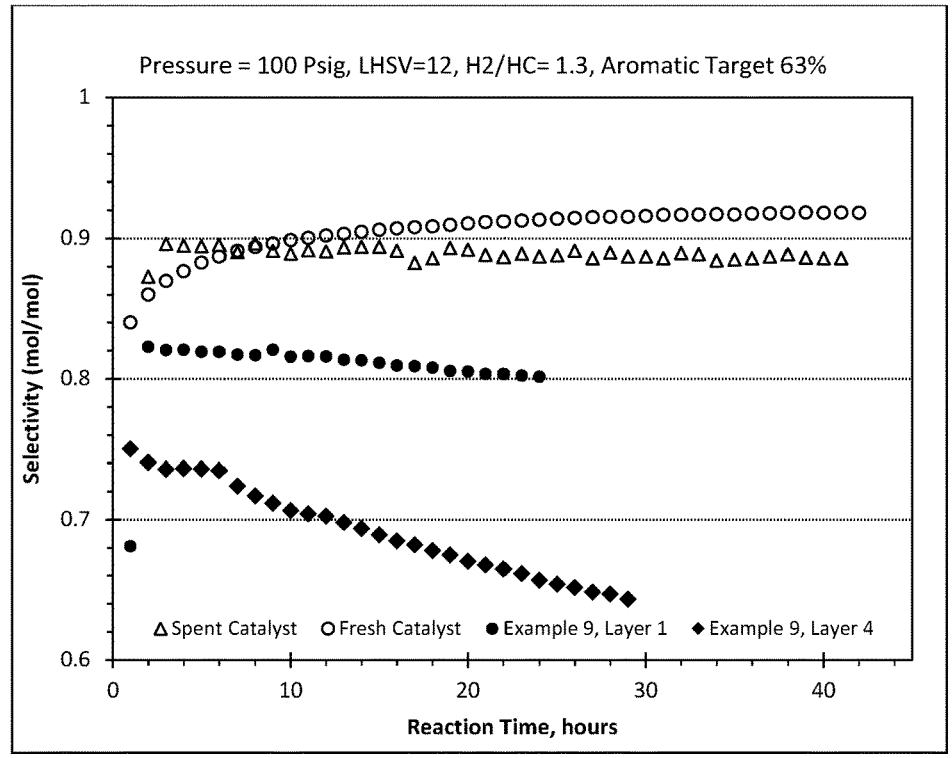
FIG. 9B presents a plot of the catalyst selectivity versus reaction time for the regenerated catalyst of Example 9, compared with the fresh catalyst and spent catalyst.

Example 9 was performed similarly to that of Example 1, except that the sequence of the halogenation steps were reversed (fluorination, carbon burn, chlorination). FIG. 9A and FIG. 9B are plots of the yield adjusted temperature versus reaction time and the selectivity versus reaction time, respectively, for the regenerated catalyst of Example 9 compared with the fresh catalyst and spent catalyst. Surprisingly, the spent catalyst could not be regenerated using the method of Example 9; note the high carbon levels in Table I. In the regeneration process of Example 9, the opposite halogen sequence to that of Example 1 (and Example 7) was used, and these results demonstrates the unexpected advantage of adding chlorine before the carbon burn (Examples 1 and 7), instead of adding fluorine before the carbon burn step, in a metal reactor.

Figure 10A:
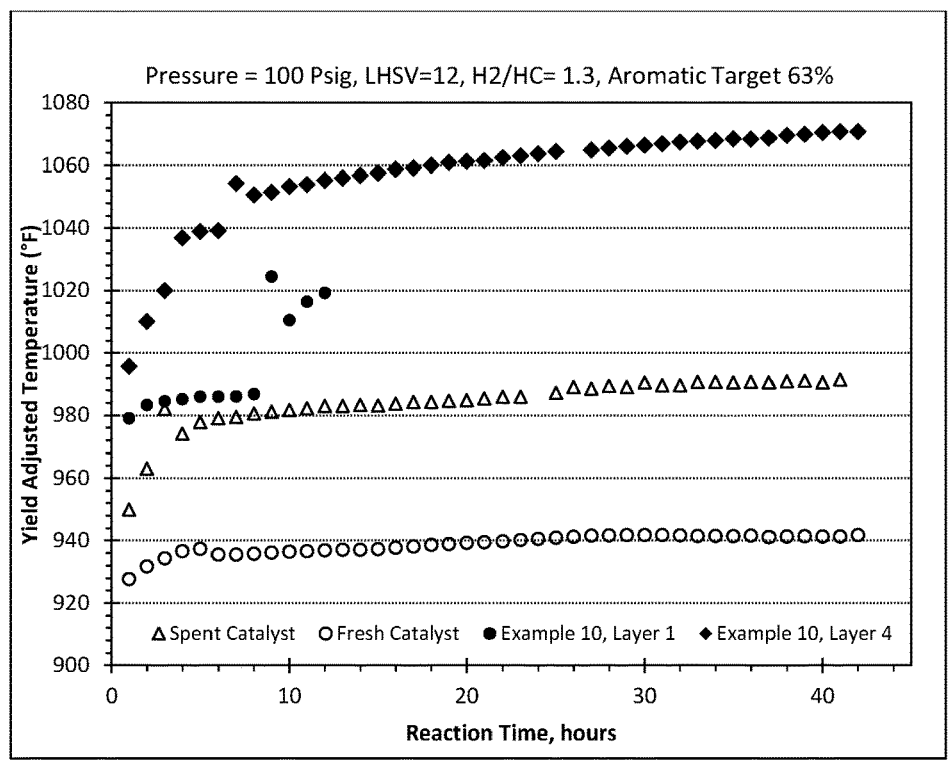
FIG. 10A presents a plot of the yield adjusted temperature versus reaction time for the regenerated catalyst of Example 10, compared with the fresh catalyst and spent catalyst.
Figure 10B:
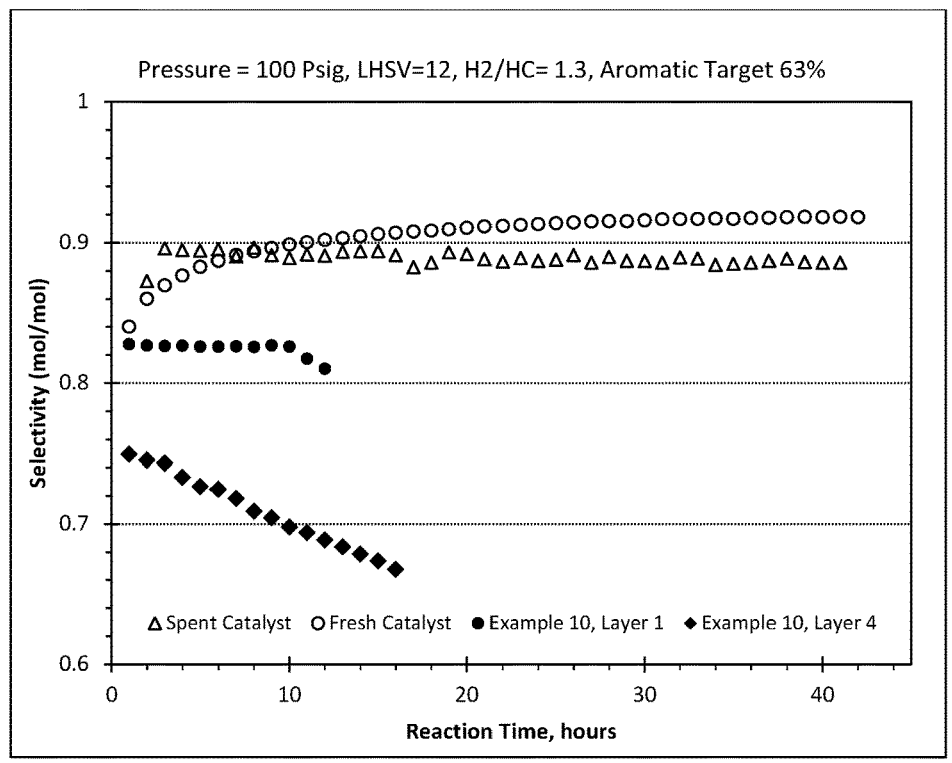
FIG. 10B presents a plot of the catalyst selectivity versus reaction time for the regenerated catalyst of Example 10, compared with the fresh catalyst and spent catalyst.

Example 10 was performed similarly to that of Example 1, except that both halogenations steps were performed prior to carbon burn (chlorination, fluorination, carbon burn). FIG. 10A and FIG. 10B are plots of the yield adjusted temperature versus reaction time and the selectivity versus reaction time, respectively, for the regenerated catalyst of Example 10 compared with the fresh catalyst and spent catalyst. Surprisingly, the spent catalyst could not be regenerated in a metal reactor using the method of Example 10; note the high carbon levels in Table 1. This example demonstrates the unexpected advantage of fluorination after the carbon burn step (Examples 1 and 7), instead of adding fluorine before the carbon burn step, without using a co-impregnation step.

Example 11 was performed using the same procedure as that of Example 1, except that the chlorination and fluorination steps were conducted at 75° F. instead of 400° F. Catalyst activity and selectivity were similar to that of Example 7, but the regenerated catalyst of Example 11 had slightly lower iron content, likely due to less corrosivity at the lower chlorination and fluorination temperatures.

In sum, these examples demonstrate that, unexpectedly, the best regeneration procedure—in terms of overall catalyst performance and reduced corrosivity in a metal reactor—utilized a step of chlorinating the spent catalyst, followed by decoking the chlorinated spent catalyst, and then fluorinating the de-coked catalyst. While not wishing to be bound by the following theory, chlorine addition before the decoking step may improve the platinum dispersion, as demonstrated by comparing Example 2 and Example 4, resulting in superior catalyst activity and selectivity. Additionally, by comparing Example 7 and Example 9, the benefits of an initial chlorination step and a final fluorination step is apparent (Example 7); the reversed sequence of Example 9 resulted in unacceptably poor catalyst activity and selectivity, and no appreciable removal of carbon from the spent catalyst. Moreover, it was also found that initial, intermediate, and/or final nitrogen purge steps may also help protect the reactor metallurgy and reduce the corrosivity of the catalyst regeneration process.

TABLE I

| Example | Layer | Cl (wt. %) | F (wt. %) | Fe (ppmw) | Carbon (wt. %) | Pt Dispersion (%) | TSOR (° F.) | TEOR (° F.) | FR (° F./hr) | $H_2 + C_5^+$ (wt. %) | Aromatics Yield (wt. %) |
|---|---|---|---|---|---|---|---|---|---|---|---|
| Spent | Composite | 0.15 | 0.06 | 172 | 1.35 | 45 | 979 | 990 | 0.30 | 90.7 | 63.1 |
| 2 | Layer 1 | 0.76 | 2.47 | 202 | 1.22 | 24.5 | — | — | — | — | — |
|   | Layer 2 | 0.93 | 0.47 | 179 | 1.24 | — | — | — | — | — | — |
|   | Layer 3 | 0.77 | 0.27 | 180 | 1.34 | — | — | — | — | — | — |
|   | Layer 4 | 0.62 | 0.19 | 193 | 1.34 | 46.0 | 956 | 964 | 0.22 | 93.6 | 63.6 |
| 3 | Layer 1 | — | — | — | 0.64 | 46.1 | — | — | — | — | — |
|   | Layer 2 | — | — | — | 0.63 | — | — | — | — | — | — |
|   | Layer 3 | — | — | — | 0.70 | — | — | — | — | — | — |
|   | Layer 4 | — | — | — | 0.51 | 46.1 | 980 | 994 | 0.36 | 90.3 | 63.6 |
| 4 | Layer 1 | 0.70 | — | 215 | 0.38 | 59.2 | — | — | — | — | — |

TABLE I-continued

| Example | Layer | Cl (wt. %) | F (wt. %) | Fe (ppmw) | Carbon (wt. %) | Pt Dispersion (%) | TSOR (° F.) | TEOR (° F.) | FR (° F./hr) | H$_2$ + C$_5^+$ (wt. %) | Aromatics Yield (wt. %) |
|---|---|---|---|---|---|---|---|---|---|---|---|
| | Layer 2 | 0.73 | — | 209 | 0.55 | — | — | — | — | — | — |
| | Layer 3 | 0.73 | — | 217 | 0.30 | — | — | — | — | — | — |
| | Layer 4 | 0.77 | — | 220 | 0.23 | 57.4 | 949 | 965 | 0.42 | 93.8 | 63.2 |
| 5 | Layer 1 | 0.71 | 1.83 | 194 | 0.03 | — | 938 | 943 | 0.13 | 95.2 | 63.2 |
| | Layer 2 | 0.80 | 0.77 | 207 | 0.02 | — | — | — | — | — | — |
| | Layer 3 | 0.85 | 0.39 | 190 | 0.02 | — | — | — | — | — | — |
| | Layer 4 | 0.82 | 0.24 | 190 | 0.13 | — | 953 | 963 | 0.27 | 95.5 | 63.2 |
| 6 | Layer 1 | 0.77 | 2.30 | 470 | 1.05 | — | 980 | — | 0.23 | 96.2 | 36.1 |
| | Layer 2 | 0.76 | 0.61 | 352 | 1.26 | — | — | — | — | — | — |
| | Layer 3 | 0.70 | 0.34 | 276 | 1.23 | — | — | — | — | — | — |
| | Layer 4 | 0.66 | 0.16 | 230 | 1.23 | — | 1074 | — | 0.16 | 82.5 | 10.7 |
| 7 | Layer 1 | 0.86 | 2.29 | 200 | 0.10 | — | 955 | 960 | 0.09 | 95.1 | 63.4 |
| | Layer 2 | 0.95 | 1.06 | 189 | 0.07 | — | — | — | — | — | — |
| | Layer 3 | 0.95 | 0.62 | 190 | 0.08 | — | — | — | — | — | — |
| | Layer 4 | 0.94 | 0.12 | 195 | 0.12 | — | 945 | 946 | 0.05 | 95.7 | 62.9 |
| 8 | Layer 1 | 0.76 | 2.45 | 222 | 0.20 | — | — | — | — | — | — |
| | Layer 2 | 0.87 | 0.74 | 206 | 0.10 | — | — | — | — | — | — |
| | Layer 3 | 0.88 | 0.58 | 184 | 0.15 | — | — | — | — | — | — |
| | Layer 4 | 0.90 | 0.41 | 186 | 0.20 | — | 940 | 942 | 0.07 | 95.4 | 62.9 |
| 9 | Layer 1 | 0.16 | 0.07 | 171 | 1.37 | — | 1040 | — | — | — | — |
| | Layer 2 | 0.15 | 0.04 | 175 | 1.29 | — | — | — | — | — | — |
| | Layer 3 | 0.14 | 0.04 | 172 | 1.24 | — | — | — | — | — | — |
| | Layer 4 | 0.14 | ND | 171 | 1.34 | — | 1045 | — | — | — | — |
| 10 | Layer 1 | 0.15 | 0.05 | 172 | 1.46 | — | 1100 | — | — | — | — |
| | Layer 2 | 0.15 | 0.05 | 181 | 1.34 | — | — | — | — | — | — |
| | Layer 3 | 0.15 | 0.04 | 184 | 1.38 | — | — | — | — | — | — |
| | Layer 4 | 0.15 | 0.04 | 172 | 1.20 | — | 1050 | — | — | — | — |

The invention is described above with reference to numerous aspects and specific examples. Many variations will suggest themselves to those skilled in the art in light of the above detailed description. All such obvious variations are within the full intended scope of the appended claims. Other aspects of the invention may include, but are not limited to, the following (aspects are described as "comprising" but, alternatively, may "consist essentially of" or "consist of"):

Aspect 1. A reforming method comprising:

(A) contacting a hydrocarbon feed with an aromatization catalyst comprising a transition metal and a catalyst support under reforming conditions in a metal reactor system to produce an aromatic product;

(B) performing step (A) for a time period sufficient to form a spent catalyst;

(C) contacting the spent catalyst with a chlorine-containing stream comprising a chlorine-containing compound to produce a chlorinated spent catalyst;

(D) contacting the chlorinated spent catalyst with a decoking gas stream comprising oxygen to produce a de-coked catalyst; and (E) contacting the de-coked catalyst with a fluorine-containing steam comprising a fluorine-containing compound.

Aspect 2. The method defined in aspect 1, wherein the reforming method is an in situ process, for example, steps (A)-(E) are performed in the same reactor system.

Aspect 3. The method defined in aspect 1, wherein steps (C)-(E) are performed externally to the reactor system of steps (A)-(B), for example, steps (C)-(E) are performed in a metal reactor that is not in the reforming reactor system.

Aspect 4. The method defined in any of aspects 1-3, further comprising a step of reactivating the catalyst after step (E).

Aspect 5. A method of regenerating a spent catalyst comprising a transition metal and a catalyst support in a metal reactor, the method comprising:

(1) contacting the spent catalyst with a chlorine-containing stream comprising a chlorine-containing compound to produce a chlorinated spent catalyst;

(2) contacting the chlorinated spent catalyst with a decoking gas stream comprising oxygen to produce a de-coked catalyst; and (3) contacting the de-coked catalyst with a fluorine-containing stream comprising a fluorine-containing compound.

Aspect 6. The method defined in any of the preceding aspects, wherein the fluorine-containing stream comprises (or consists essentially of, or consists of) the fluorine-containing compound and any inert gas disclosed herein, for example, nitrogen.

Aspect 7. The method defined in any of the preceding aspects, wherein the fluorine-containing stream comprises (or consists essentially of, or consists of) fluorine gas (F$_2$) and nitrogen.

Aspect 8. The method defined in any of the preceding aspects, wherein the amount of fluorine-containing compound in the fluorine-containing stream is controlled to give a concentration of fluorine (F) less than any maximum amount or in any range disclosed herein, for example, less than about 50,000 ppmv, in a range from about 50 to about 25,000 ppmv, or in a range from about 1000 to about 15,000 ppmv.

Aspect 9. The method defined in any of the preceding aspects, wherein the fluorine-containing stream is substantially free of oxygen-containing compounds and/or chlorine-containing compounds, for example, less than 100 ppmw.

Aspect 10. The method defined in any of the preceding aspects, wherein the fluorination step is conducted at a fluorination temperature in any fluorination temperature range disclosed herein, for example, from about 0° C. to about 300° C., from about 20° C. to about 250° C., or from about 15° C. to about 50° C.

Aspect 11. The method defined in any of the preceding aspects, wherein the fluorination step is conducted for a time period in any range of fluorination time periods disclosed herein, for example, from about 1 to about 48 hours, from about 1 to about 12 hours, or from about 2 to about 8 hours.

Aspect 12. The method defined in any of the preceding aspects, wherein the chlorine-containing stream comprises (or consists essentially of, or consists of) the chlorine-containing compound and any inert gas disclosed herein, for example, nitrogen.

Aspect 13. The method defined in any of the preceding aspects, wherein the chlorine-containing stream comprises (or consists essentially of, or consists of) chlorine gas ($Cl_2$) and nitrogen.

Aspect 14. The method defined in any of the preceding aspects, wherein the amount of chlorine-containing compound in the chlorine-containing stream is controlled to give a concentration of chlorine (Cl) less than any maximum amount or in any range disclosed herein, for example, less than about 50,000 ppmv, in a range from about 50 to about 25,000 ppmv, or in a range from about 5,000 to about 25,000 ppmv.

Aspect 15. The method defined in any of the preceding aspects, wherein the chlorine-containing stream is substantially free of oxygen-containing compounds and/or fluorine-containing compounds, for example, less than 100 ppmw.

Aspect 16. The method defined in any of the preceding aspects, wherein the chlorination step is conducted at a chlorination temperature in any chlorination temperature range disclosed herein, for example, from about 0° C. to about 500° C., from about 20° C. to about 300° C., or from about 100° C. to about 250° C.

Aspect 17. The method defined in any of the preceding aspects, wherein the chlorination step is conducted for a time period in any range of chlorination time periods disclosed herein, for example, from about 1 to about 48 hours, from about 1 to about 12 hours, or from about 2 to about 8 hours.

Aspect 18. The method defined in any of the preceding aspects, wherein the decoking gas stream comprises (or consists essentially of, or consists of) any combination of an inert gas (one or more) and oxygen disclosed herein, for example, a mixture of nitrogen and oxygen, air, or a mixture of air and nitrogen.

Aspect 19. The method defined in any of the preceding aspects, wherein the decoking gas stream comprises a mole % of oxygen less than any maximum amount or in any range disclosed herein, for example, less than about 5 mole %, in a range from about 0.1 to about 10 mole %, or in a range from about 0.5 to about 3 mole %.

Aspect 20. The method defined in any of the preceding aspects, wherein the decoking gas stream is substantially free of halogen-containing compounds (e.g., substantially halogen-free, substantially chlorine-free), for example, less than 100 ppmw.

Aspect 21. The method defined in any of the preceding aspects, wherein the decoking gas stream is substantially free of water, for example, less than 100 ppmw.

Aspect 22. The method defined in any of the preceding aspects, wherein the carbon burn step is conducted at a peak decoking temperature in any peak decoking temperature range disclosed herein, for example, from about 150° C. to about 600° C., from about 200° C. to about 500° C., or from about 350° C. to about 450° C.

Aspect 23. The method defined in any of the preceding aspects, wherein the carbon burn step is started at an initial decoking temperature which is the same as any chlorine purging temperature disclosed herein, for example, from about 0° C. to about 300° C., from about 20° C. to about 250° C., or from about 50° C. to about 200° C.

Aspect 24. The method defined in any of the preceding aspects, wherein the carbon burn step is conducted for a time period in any range of de-coking time periods disclosed herein, for example, from about 1 to about 72 hours, from about 12 to about 48 hours, or from about 1 to about 6 hours.

Aspect 25. The method defined in any of the preceding aspects, wherein the carbon burn step is conducted for a time period sufficient to reduce the wt. % of carbon on the chlorinated spent catalyst to less than any maximum weight percentage of carbon disclosed herein, for example, less than about 1 wt. %, less than about 0.5 wt. %, or less than about 0.2 wt. %.

Aspect 26. The method defined in any of the preceding aspects, wherein the method further comprises a partial decoking step prior to the chlorination step, the partial decoking step comprising contacting the spent catalyst with a partial decoking gas stream comprising oxygen.

Aspect 27. The method defined in aspect 26, wherein the partial decoking gas stream comprises (or consists essentially of, or consists of) any combination of an inert gas (one or more) and oxygen disclosed herein, for example, a mixture of nitrogen and oxygen, or air.

Aspect 28. The method defined in any of aspects 26-27, wherein the partial decoking gas stream comprises a mole % of oxygen less than any maximum amount or in any range disclosed herein, for example, less than about 5 mole %, or in a range from about 0.5 to about 3 mole %.

Aspect 29. The method defined in any of aspects 26-28, wherein the partial decoking gas stream is substantially free of halogen-containing compounds (e.g., substantially halogen-free), for example, less than 100 ppmw.

Aspect 30. The method defined in any of aspects 26-29, wherein the decoking gas stream is substantially free of water, for example, less than 100 ppmw.

Aspect 31. The method defined in any of aspects 26-30, wherein the partial decoking step is conducted at a partial decoking temperature in any partial decoking temperature range disclosed herein, for example, from about 150° C. to about 250° C.

Aspect 32. The method defined in any of aspects 26-31, wherein the partial decoking step is conducted for a time period in any range of partial de-coking time periods disclosed herein, for example, from about 2 to about 24 hours.

Aspect 33. The method defined in any of aspects 26-32, wherein the partial decoking step is conducted for a time period sufficient to reduce the wt. % of carbon on the spent catalyst to any range of weight percentage of carbon disclosed herein, for example, from about 1 to 10 wt. %, or from about 4 to about 5 wt. %.

Aspect 34. The method defined in any of the preceding aspects, wherein the method further comprises a pre-drying step prior to the chlorination step, the pre-drying step comprising contacting the spent catalyst with a pre-drying gas stream comprising (or consisting essentially of, or consisting of) any inert gas disclosed herein, for example, nitrogen.

Aspect 35. The method defined in aspect 34, wherein the pre-drying gas stream is substantially free of oxygen-containing compounds, for example, less than 100 ppmw.

Aspect 36. The method defined in any of aspects 34-35, wherein the pre-drying step is conducted at a pre-drying temperature in any pre-drying temperature range disclosed herein, for example, from about 100° C. to about 500° C., from about 0° C. to about 400° C., or from about 180° C. to about 280° C.

Aspect 37. The method defined in any of aspects 34-36, wherein the pre-drying step is conducted for a time period in any range of pre-drying time periods disclosed herein, for example, from about 1 to about 48 hours.

Aspect 38. The method defined in any of aspects 34-37, wherein the pre-drying step is conducted for a time period sufficient to reduce the moisture content of the spent catalyst to less than any maximum moisture content of the spent catalyst disclosed herein, for example, less than about 4 wt. %, or less than about 1 wt. %.

Aspect 39. The method defined in any of the preceding aspects, wherein the method further comprises a chlorine purging step prior to the carbon burn step, the chlorine purging step comprising contacting the chlorinated spent catalyst with a chlorine purging stream comprising (or consisting essentially of, or consisting of) any inert gas disclosed herein, for example, nitrogen.

Aspect 40. The method defined in aspect 39, wherein the chlorine purging stream is substantially free of oxygen-containing compounds, for example, less than 100 ppmw.

Aspect 41. The method defined in any of aspects 39-40, wherein the chlorine purging stream is substantially free of halogen-containing compounds (substantially halogen-free), for example, less than 100 ppmw.

Aspect 42. The method defined in any of aspects 39-41, wherein the chlorine purging step is conducted at a chlorine purging temperature in any chlorine purging temperature range disclosed herein, for example, from about 0° C. to about 400° C., from about 15° C. to about 300° C., or from about 25° C. to about 250° C.

Aspect 43. The method defined in any of aspects 39-42, wherein the chlorine purging step is conducted for a time period in any range of chlorine purging time periods disclosed herein, for example, from about 1 to about 48 hours.

Aspect 44. The method defined in any of aspects 39-43, wherein the chlorine purging step is conducted for a time period sufficient to reduce the chlorine content of the outgoing chlorine purging effluent stream, after contacting the chlorinated spent catalyst, to less than any maximum chlorine content described herein, for example, less than about 100 ppmw of chlorine-containing compounds.

Aspect 45. The method defined in any of the preceding aspects, wherein the method further comprises a fluorine purging step after the fluorination step, the fluorine purging step comprising contacting the de-coked and fluorinated catalyst with a fluorine purging stream comprising (or consisting essentially of, or consisting of) any inert gas disclosed herein, for example, nitrogen.

Aspect 46. The method defined in aspect 45, wherein the fluorine purging stream is substantially free of oxygen-containing compounds, for example, less than 100 ppmw.

Aspect 47. The method defined in any of aspects 45-46, wherein the fluorine purging stream is substantially free of halogen-containing compounds (substantially halogen-free), for example, less than 100 ppmw.

Aspect 48. The method defined in any of aspects 45-47, wherein the fluorine purging step is conducted at a fluorine purging temperature in any fluorine purging temperature range disclosed herein, for example, from about 0° C. to about 400° C., from about 15° C. to about 300° C., or from about 25° C. to about 250° C.

Aspect 49. The method defined in any of aspects 45-48, wherein the fluorine purging step is conducted for a time period in any range of fluorine purging time periods disclosed herein, for example, from about 1 to about 48 hours.

Aspect 50. The method defined in any of aspects 45-49, wherein the fluorine purging step is conducted for a time period sufficient to reduce the fluorine content of the outgoing fluorine purging effluent stream, after contacting the de-coked and fluorinated catalyst, to less than any maximum fluorine content described herein, for example, less than about 100 ppmw of fluorine-containing compounds.

Aspect 51. The method defined in any of the preceding aspects, wherein the method further comprises an oxygen purging step after the carbon burn step, the oxygen purging step comprising contacting the de-coked catalyst with an oxygen purging stream comprising (or consisting essentially of, or consisting of) any inert gas disclosed herein, for example, nitrogen.

Aspect 52. The method defined in aspect 51, wherein the oxygen purging stream is substantially free of oxygen-containing compounds, for example, less than 100 ppmw.

Aspect 53. The method defined in any of aspects 51-52, wherein the oxygen purging stream is substantially free of halogen-containing compounds (substantially halogen-free), for example, less than 100 ppmw.

Aspect 54. The method defined in any of aspects 51-53, wherein the oxygen purging step is conducted at an oxygen purging temperature in any oxygen purging temperature range disclosed herein, for example, from about 0° C. to about 400° C., from about 15° C. to about 300° C., or from about 25° C. to about 250° C.

Aspect 55. The method defined in any of aspects 51-54, wherein the oxygen purging step is conducted for a time period in any range of oxygen purging time periods disclosed herein, for example, from about 1 to about 48 hours.

Aspect 56. The method defined in any of aspects 51-55, wherein the oxygen purging step is conducted for a time period sufficient to reduce the oxygen content of the outgoing oxygen purging effluent stream, after contacting the de-coked catalyst, to less than any maximum oxygen content described herein, for example, less than about 100 ppmw of oxygen-containing compounds.

Aspect 57. The method defined in any of the preceding aspects, wherein the method further comprises a hydrocarbon treatment step prior to the carbon burn step, the hydrocarbon treatment step comprising contacting the chlorinated spent catalyst with a hydrocarbon treatment stream comprising a hydrocarbon feed.

Aspect 58. The method defined in aspect 57, wherein the hydrocarbon feed comprises $C_6$-$C_8$ alkanes and/or cycloalkanes.

Aspect 59. The method defined in any of aspects 57-58, wherein the hydrocarbon treatment step is conducted at a hydrocarbon treatment temperature in any hydrocarbon treatment temperature range disclosed herein, for example, from about 400° C. to about 600° C.

Aspect 60. The method defined in any of aspects 57-59, wherein the hydrocarbon treatment step is conducted for a time period in any range of hydrocarbon treatment time periods disclosed herein, for example, from about 1 to about 48 hours.

Aspect 61. The method defined in any of the preceding aspects, wherein the method further comprises a reducing step after the fluorination step, the reducing step comprising contacting the de-coked and fluorinated catalyst with a reducing gas stream comprising (or consisting essentially of, or consisting of) molecular hydrogen.

Aspect 62. The method defined in aspect 61, wherein the reducing gas stream comprises a mole % of molecular hydrogen greater than any minimum amount or in any range disclosed herein, for example, greater than about 25 mole %, or greater than about 75 mole %.

Aspect 63. The method defined in any of aspects 61-62, wherein the reducing step is conducted at a peak reducing temperature in any peak reducing temperature range disclosed herein, for example, from about 400° C. to about 600° C.

Aspect 64. The method defined in any of aspects 61-63, wherein the reducing step is started at an initial reducing temperature which is the same as any fluorination temperature disclosed herein, for example, in a range from about 0° C. to about 300° C., from about 20° C. to about 250° C., or from about 15° C. to about 50° C.

Aspect 65. The method defined in any of aspects 61-64, wherein the reducing step is conducted for a time period in any range of reducing step time periods disclosed herein, for example, from about 10 to about 30 hours.

Aspect 66. The method defined in any of the preceding aspects, wherein the catalyst support comprises a zeolite, an amorphous inorganic oxide, or any combination thereof.

Aspect 67. The method defined in any of the preceding aspects, wherein the catalyst support comprises an L-zeolite, a Y-zeolite, a mordenite, an omega zeolite, and/or a beta zeolite.

Aspect 68. The method defined in any of the preceding aspects, wherein the catalyst support comprises a potassium L-zeolite or a barium ion-exchanged L-zeolite.

Aspect 69. The method defined in any of the preceding aspects, wherein the catalyst support comprises a binder comprising alumina, silica, a mixed oxide thereof, or a mixture thereof.

Aspect 70. The method defined in any of the preceding aspects, wherein the transition metal comprises a Group 8-11 transition metal.

Aspect 71. The method defined in any of the preceding aspects, wherein the transition metal comprises platinum.

Aspect 72. The method defined in any of the preceding aspects, wherein the catalyst comprises any weight percentage range of transition metal disclosed herein, for example, from about 0.1 wt. % to about 10 wt. %, or from about 0.3 wt. % to about 5 wt. %, transition metal.

Aspect 73. The method defined in any of the preceding aspects, wherein the spent catalyst comprises any weight percentage range of platinum disclosed herein, for example, from about 0.1 wt. % to about 10 wt. %, or from about 0.5 wt. % to about 2 wt. %, platinum.

Aspect 74. The method defined in any of the preceding aspects, wherein the catalyst comprises platinum on a KL-zeolite.

Aspect 75. The method defined in any of the preceding aspects, wherein the catalyst further comprises chlorine and fluorine.

Aspect 76. The method defined in aspect 75, wherein the catalyst comprises any weight percentage range of chlorine and/or weight percentage range of fluorine disclosed herein, for example, from about 0.01 wt. % to about 5 wt. %, or from about 0.3 to about 1.3 wt. % fluorine, and/or from about 0.01 wt. % to about 5 wt. %, or from about 0.3 to about 1.3 wt. % chlorine.

Aspect 77. The method defined in any of aspects 75-76, wherein the catalyst comprises any molar ratio of chlorine:fluorine disclosed herein, for example, from about 0.5:1 to about 4:1.

Aspect 78. The method defined in any of the preceding aspects, wherein the chlorine-containing compound comprises hydrochloric acid, chlorine gas ($Cl_2$), carbon tetrachloride, tetrachloroethylene, chlorobenzene, methyl chloride, methylene chloride, chloroform, allyl chloride, trichloroethylene, a chloramine, a chlorine oxide, a chlorine acid, chlorine dioxide, dichlorine monoxide, dichlorine heptoxide, chloric acid, perchloric acid, ammonium chloride, tetramethylammonium chloride, tetraethylammonium chloride, tetrapropylammonium chloride, tetrabutylammonium chloride, methyltriethylammonium chloride, or any combination thereof.

Aspect 79. The method defined in any of the preceding aspects, wherein the chlorine-containing compound comprises chlorine gas ($Cl_2$).

Aspect 80. The method defined in any of the preceding aspects, wherein the fluorine-containing compound comprises hydrofluoric acid, fluorine gas, 2,2,2-trifluoroethanol, tetrafluoroethylene, carbon tetrafluoride, carbon trifluoride, fluoromethane, heptafluoropropane, decafluorobutane, hexafluoroisopropanol, tetrafluoropropanol, pentafluoropropanol, hexafluorophenylpropanol, perfluorobutyl alcohol, hexafluor-2-propanol, pentafluoro-1-propanol, tetrafluoro-1-propanol, 1,1,1,3,3,3-hexafluoro-2-propanol, 2,2,3,3,3-pentafluoro-1-propanol, ammonium fluoride, tetramethylammonium fluoride, tetraethylammonium fluoride, tetrapropylammonium fluoride, tetrabutylammonium fluoride, methyltriethylammonium fluoride or any combination thereof.

Aspect 81. The method defined in any of the preceding aspects, wherein the fluorine-containing compound comprises fluorine gas ($F_2$).

Aspect 82. A reactivated catalyst or a regenerated catalyst produced by the method defined in any one of the preceding aspects.

Aspect 83. The reactivated catalyst or regenerated catalyst defined in aspect 82, wherein the reactivated catalyst or regenerated catalyst comprises any amount of iron disclosed herein, for example, less than about 400 ppmw, less than about 300 ppmw, less than about 250 ppmw, from about 5 ppmw to about 400 ppmw, from about 50 ppmw to about 300 ppmw, or from about 50 ppmw to about 250 ppmw iron.

Aspect 84. The reactivated catalyst or regenerated catalyst defined in any one of aspects 82-83, wherein the reactivated catalyst or regenerated catalyst comprises any amount of carbon disclosed herein, for example, less than about 1 wt. %, less than about 0.5 wt. %, from about 0.01 wt. % to about 1 wt. %, from about 0.01 wt. % to about 0.5 wt. %, or from about 0.02 wt. % to about 0.5 wt. % carbon.

Aspect 85. The reactivated catalyst or regenerated catalyst defined in any one of aspects 82-84, wherein the reactivated catalyst or regenerated catalyst comprises any amount of chlorine disclosed herein, for example, from about 0.01 wt. % to about 5 wt. %, from about 0.05 wt. % to about 3 wt. %, or from about 0.3 wt. % to about 1.3 wt. % chlorine.

Aspect 86. The reactivated catalyst or regenerated catalyst defined in any one of aspects 82-85, wherein the reactivated catalyst or regenerated catalyst comprises any amount of fluorine disclosed herein, for example, from about 0.01 wt. % to about 5 wt. %, from about 0.05 wt. % to about 3 wt. %, or from about 0.3 wt. % to about 1.3 wt. % fluorine.

Aspect 87. The reactivated catalyst or regenerated catalyst defined in any one of aspects 82-86, wherein the reactivated catalyst or regenerated catalyst is characterized by a TEOR within about 50° F., within about 40° F., within about 30° F., or within about 20° F., of the TEOR of a fresh reference catalyst.

Aspect 88. The reactivated catalyst or regenerated catalyst defined in any one of aspects 82-87, wherein the reactivated catalyst or regenerated catalyst is characterized by a TSOR within about 50° F., within about 40° F., within about 30° F., or within about 20° F., of the TSOR of a fresh reference catalyst.

Aspect 89. The reactivated catalyst or regenerated catalyst defined in any one of aspects 82-88, wherein the reactivated catalyst or regenerated catalyst is characterized by a fouling rate (FR) in any range disclosed herein, for example, from about 0.01° F./hr to about 0.25° F./hr, from about 0.02° F./hr to about 0.2° F./hr, from about 0.03° F./hr to about 0.2° F./hr, or from about 0.03° F./hr to about 0.15° F./hr.

Aspect 90. The reactivated catalyst or regenerated catalyst defined in any one of aspects 82-89, wherein the reactivated catalyst or regenerated catalyst is characterized by a benzene+toluene selectivity in any selectivity range disclosed herein, for example, from about 0.88 to about 0.95, or from about 0.89 to about 0.94.

Aspect 91. The method or catalyst defined in any of the preceding aspects, wherein the metal reactor (or metal reactor system) comprises stainless steel.

I claim:

1. A method of regenerating a spent catalyst comprising a transition metal and a catalyst support in a metal reactor, the method comprising:
   (1) contacting the spent catalyst with a chlorine-containing stream comprising a chlorine-containing compound to produce a chlorinated spent catalyst;
   (2) contacting the chlorinated spent catalyst with a decoking gas stream comprising oxygen to produce a de-coked catalyst; and
   (3) contacting the de-coked catalyst with a fluorine-containing stream comprising a fluorine-containing compound to form a regenerated catalyst containing less than about 1 wt. % of carbon; wherein:
   the transition metal comprises a Group 8-11 transition metal;
   the catalyst support comprises a large pore zeolite having an average pore diameter in a range of from about 7 Å to about 12 Å; and
   the spent catalyst further comprises chlorine and/or fluorine.

2. The method of claim 1, wherein step (1) is conducted at a chlorination temperature in a range from about 20° C. to about 300° C.

3. The method of claim 1, wherein an amount of the chlorine-containing compound in the chlorine-containing stream is controlled to give a concentration of chlorine (Cl) in the chlorine-containing stream in a range from about 5,000 to about 50,000 ppm by volume.

4. The method of claim 3, wherein the chlorine-containing stream is substantially free of an oxygen-containing compound.

5. The method of claim 1, wherein the chlorine-containing stream comprises $Cl_2$ and nitrogen.

6. The method of claim 1, further comprising a chlorine purging step prior to step (2), the chlorine purging step comprising contacting the chlorinated spent catalyst with a chlorine purging stream consisting essentially of an inert gas.

7. The method of claim 1, wherein:
   step (2) is conducted at a peak decoking temperature in a range from about 300° C. to about 500° C.;
   the decoking gas stream comprises nitrogen and oxygen; and
   the decoking gas stream is substantially free of halogen-containing compounds.

8. The method of claim 1, wherein step (3) is conducted at a fluorination temperature in a range from about 20° C. to about 250° C.

9. The method of claim 1, wherein an amount of the fluorine-containing compound in the fluorine-containing stream is controlled to give a concentration of fluorine (F) in the fluorine-containing stream is in a range from about 5,000 to about 100,000 ppm by volume.

10. The method of claim 9, wherein the fluorine-containing stream is substantially free of oxygen-containing compounds.

11. The method of claim 1, wherein the fluorine-containing stream comprises $F_2$ and nitrogen.

12. The method of claim 1, further comprising a fluorine purging step after step (3), the fluorine purging step comprising contacting the regenerated catalyst with a fluorine purging stream consisting essentially of an inert gas.

13. The method of claim 1, wherein the spent catalyst comprises:
   platinum on the catalyst support, wherein the catalyst support comprises a KL-zeolite and a binder comprising alumina, silica, a mixed oxide thereof, or a mixture thereof;
   from about 0.01 wt. % to about 5 wt. % chlorine; and
   from about 0.01 wt. % to about 5 wt. % fluorine.

14. The method of claim 1, further comprising a reducing step after step (3), the reducing step comprising contacting the regenerated catalyst with a reducing gas stream comprising molecular hydrogen.

15. The method of claim 1, wherein the metal reactor comprises a stainless steel, and the regenerated catalyst contains less than about 250 ppmw of iron and less than about 0.5 wt. % of carbon.

16. The method of claim 15, wherein the regenerated catalyst is characterized by:
   a TEOR (end of run temperature) within about 40° F. of the TEOR of a fresh reference catalyst;
   a FR (fouling rate) in a range from about 0.02° F./hr to about 0.2° F./hr; and
   a benzene+toluene selectivity in a range from about 0.88 to about 0.95.

17. A method of regenerating a spent catalyst comprising a transition metal and a catalyst support in a metal reactor, the method comprising:
   (i) contacting the spent catalyst with a chlorine-containing stream comprising a chlorine-containing compound to produce a chlorinated spent catalyst;
   (ii) contacting the chlorinated spent catalyst with a chlorine purging stream comprising an inert gas;
   (iii) contacting the chlorinated spent catalyst with a decoking gas stream comprising oxygen to produce a de-coked catalyst;
   (iv) contacting the de-coked catalyst with a fluorine-containing stream comprising a fluorine-containing compound to produce a de-coked and fluorinated catalyst; and
   (v) contacting the de-coked and fluorinated catalyst with a fluorine purging stream comprising an inert gas to form a regenerated catalyst containing less than about 1 wt. % of carbon; wherein:
   the transition metal comprises a Group 8-11 transition metal;
   the catalyst support comprises a large pore zeolite having an average pore diameter in a range of from about 7 Å to about 12 Å; and
   the spent catalyst further comprises chlorine and/or fluorine.

18. The method of claim 17, wherein:
   the chlorine-containing stream comprises $Cl_2$ and nitrogen;
   the chlorine purging stream consists essentially of nitrogen;
   the decoking gas stream comprises nitrogen and oxygen;

the fluorine-containing stream comprises $F_2$ and nitrogen; and the fluorine purging stream consists essentially of nitrogen.

19. The method of claim 17, further comprising an oxygen purging step after step (iii) and before step (iv), the oxygen purging step comprising contacting the de-coked catalyst with an oxygen purging stream consisting essentially of an inert gas.

20. The method of claim 17, further comprising a reducing step after step (v), the reducing step comprising contacting the regenerated catalyst with a reducing gas stream comprising molecular hydrogen to produce a reactivated catalyst.

21. The method of claim 20, wherein the reactivated catalyst contains less than about 300 ppmw of iron and less than about 0.5 wt. % of carbon, and is characterized by:
- a TEOR (end of run temperature) within about 40° F. of the TEOR of a fresh reference catalyst;
- a FR (fouling rate) in a range from about 0.02° F./hr to about 0.2° F./hr; and
- a benzene +toluene selectivity in a range from about 0.88 to about 0.95.

22. A reforming process comprising:
(A) contacting a hydrocarbon feed with an aromatization catalyst comprising a transition metal and a catalyst support under reforming conditions in a metal reactor system to produce an aromatic product;

(B) performing step (A) for a time period sufficient to form a spent catalyst;

(C) contacting the spent catalyst with a chlorine-containing stream comprising a chlorine-containing compound to produce a chlorinated spent catalyst;

(D) contacting the chlorinated spent catalyst with a decoking gas stream comprising oxygen to produce a de-coked catalyst; and (E) contacting the de-coked catalyst with a fluorine-containing stream comprising a fluorine-containing compound to form a regenerated catalyst containing less than about 1 wt. % of carbon; wherein:

the transition metal comprises a Group 8-11 transition metal;

the catalyst support comprises a large pore zeolite having an average pore diameter in a range of from about 7 Å to about 12 Å;

the aromatization catalyst further comprises chlorine and/or fluorine, and wherein steps (C)-(E) are performed in a metal reactor.

23. The process of claim 22, wherein the reforming process is an in situ process.

24. The process of claim 22, wherein steps (C)-(E) are performed in a metal reactor external to the metal reactor system.

* * * * *